United States Patent
Nagaoka et al.

(10) Patent No.: US 7,727,472 B2
(45) Date of Patent: Jun. 1, 2010

(54) CHEMICAL ANALYSIS APPARATUS AND CHEMICAL ANALYSIS CARTRIDGE

(75) Inventors: Yoshihiro Nagaoka, Ishioka (JP); Nobuyuki Maki, Tsuchiura (JP); Noriyo Nishijima, Abiko (JP); Michihiro Saito, Kashiwa (JP); Hiroki Ihara, Shiroi (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1141 days.

(21) Appl. No.: 11/319,977

(22) Filed: Dec. 29, 2005

(65) Prior Publication Data

US 2006/0153735 A1     Jul. 13, 2006

(30) Foreign Application Priority Data

Jan. 7, 2005   (JP)  ............... 2005-002647

(51) Int. Cl.
  *G01N 15/06* (2006.01)
  *G01N 33/00* (2006.01)
  *G01N 33/48* (2006.01)

(52) U.S. Cl. .................. 422/68.1; 422/50; 422/72; 422/100; 422/101; 435/287.2; 436/43; 436/45; 436/63; 436/174

(58) Field of Classification Search .......... 422/64, 422/50, 68.1, 55, 58, 100–104; 435/287.2; 436/47, 43, 45, 63, 174, 177, 180
See application file for complete search history.

(56) References Cited

U.S. PATENT DOCUMENTS

| 4,876,203 | A | 10/1989 | Guigan |
| 6,706,519 | B1 | 3/2004 | Kellogg et al. |
| 2002/0039783 | A1 | 4/2002 | McMillan et al. |
| 2003/0211010 | A1 | 11/2003 | Nagaoka et al. |
| 2004/0217069 | A1 | 11/2004 | Columbus |

FOREIGN PATENT DOCUMENTS

| EP | 1 459 795 | 9/2004 |
| EP | 1 464 398 | 10/2004 |
| EP | 1 503 209 | 2/2005 |
| JP | 2001-527220 | 12/2001 |
| JP | 2003-502656 | 1/2003 |

*Primary Examiner*—Tony G Soohoo
*Assistant Examiner*—Robert Eom
(74) *Attorney, Agent, or Firm*—Antonelli, Terry, Stout & Kraus, LLP.

(57) ABSTRACT

A chemical analysis apparatus comprises a motor, a holding disk that can be rotated by the motor, a plurality of examination cartridges arranged on the holding disk, a perforator that perforates the examination cartridges, a heating device, and a detection device. The examination cartridge comprises a substrate including a vessel and a flow channel, which are defined by recesses, and a cover that covers the vessel and the flow channel. A centrifugal force generated by rotation of the holding disk is made use of to move a solution from a vessel on an inner peripheral side relative to an axis of rotation to a vessel on an outer peripheral side relative to the axis of rotation through the flow channel.

8 Claims, 18 Drawing Sheets

CHEMICAL ANALYSIS APPARATUS AND CHEMICAL ANALYSIS CARTRIDGE

BACKGROUND OF THE INVENTION

The present invention relates to a chemical analysis apparatus that makes use of a centrifugal force to cause movement, mixing, etc. of a solution, and more particular, to a chemical analysis apparatus that uses a removable cartridge.

As a method of extracting DNA from a liquid specimen containing DNA, JP-A-2003-502656 describes an apparatus for and a method of conducting in vitro amplifying assay as miniaturized. In this apparatus, after a DNA mixing liquid is passed through a glass filter as an inorganic substrate, a washing liquid and an eluant are passed therethrough and only DNA is recovered. The glass filter is provided on a rotatable structure and reagents such as a washing liquid, an eluant, etc. are held in respective reagent reservoirs in the same structure. A centrifugal force generated upon rotation of the structure causes the respective reagents to flow, and valves provided in minute flow channels, which interconnect the respective reagent reservoirs and the glass filter, are opened whereby the reagents pass through the glass filter.

As a chemical analysis apparatus that extracts and analyzes a specific chemical substance, such as a nucleic acid, etc., from a specimen containing a plurality of chemical substances, JP-A-2001-527220 describes an integral type fluid operation cartridge. In this apparatus, an integral type cartridge comprises therein a trap component part that traps reagents such as a solution, a washing liquid, an eluant, etc., and a nucleic acid, and after a specimen containing a nucleic acid is injected into the cartridge, the specimen and the eluant are mixed with each other and passed through the trap component part, a washing liquid is further passed through the trap component part, an eluant is further passed through the trap component part, and the eluant having passed through the trap component part is brought into contact with a PCR reagent to make it flow to a reaction chamber.

However, the apparatus described in the JP-A-2003-502656 involves a possibility that the reagents having passed remain in the valve parts to contaminate the recovered DNA because wax, etc., melting when heated is used for the valves. That is, there is a possibility that a DNA mixing liquid and a washing liquid remain in the valve parts and the DNA mixing liquid and the washing liquid remaining in the valve parts flow into the glass filter during a process, in which a centrifugal force causes an eluant to pass through the glass filter.

Also, with the integral type fluid operation cartridge described in the JP-A-2001-527220, reagents are passed through the trap component part by opening valves, etc. provided in the minute flow channels, which interconnect the respective reagent chambers and the trap component part, when using a pump to feed the respective reagents. Further, valves or the like provided between the trap component part and the respective chambers switch so that, out of reagents having passed through the trap component part, the washing liquid flows to a waste-liquid chamber and the eluant flows to a reaction chamber. In case of feeding a plurality of reagents by means of the pump, the reagents may remain on flow channel walls, and liquids are liable to remain especially when there are present obstacles such as valves, etc. Once the liquids remain, they do not flow, and therefore, there is a possibility of contamination at those parts, at which the liquids join other reagents. Also, in the case where a washing liquid and an eluant, which have passed through the trap component part, are switched over by valves, etc. to make them flow to separate chambers, the washing liquid having earlier flowed to the waste-liquid chamber contaminates flow channels upstream of the valves, etc., for switchover to the reaction chamber, so that there is a fear of mixing of the washing liquid with the eluant.

BRIEF SUMMARY OF THE INVENTION

It is an object of the invention to provide a simple chemical analysis apparatus that can solve at least one of the problems described above and extracts and detects a specific chemical substance in a liquid specimen with high accuracy.

A chemical analysis apparatus comprises a motor, a holding disk that can be rotated by the motor, a plurality of examination cartridges arranged on the holding disk, a perforator that perforates the examination cartridges, a heating device, and a detection device. The examination cartridge comprises a substrate including a vessel and a flow channel, which are defined by recesses. A cover that covers the vessel and the flow channel is mounted on the substrate. A centrifugal force generated by rotation of the holding disk is made use of to move a solution from a vessel on an inner peripheral side relative to an axis of rotation to a vessel on an outer peripheral side relative to the axis of rotation through the flow channel.

That flow channel, through which a solution is moved from the vessel on the inner peripheral side to the vessel on the outer peripheral side, terminates at an inner peripheral end of the vessel on the outer peripheral side via a return portion starting from an inner peripheral end of the vessel on the inner peripheral side, extending toward the inner peripheral side, and again extending toward the outer peripheral side. The examination cartridge is provided with an air flow channel and a vent hole, and the cover that covers the vent hole is perforated whereby the vessel is communicated with the atmosphere through the vent hole and the air flow channel.

The invention can provide an analysis apparatus and an analysis structure, which are of high performance and can suppress contamination between reagents in the case where valve components and a plurality of reagents are involved.

Other objects, features and advantages of the invention will become apparent from the following description of the embodiments of the invention taken in conjunction with the accompanying drawings.

DETAILED DESCRIPTION OF THE INVENTION

Figure 1:
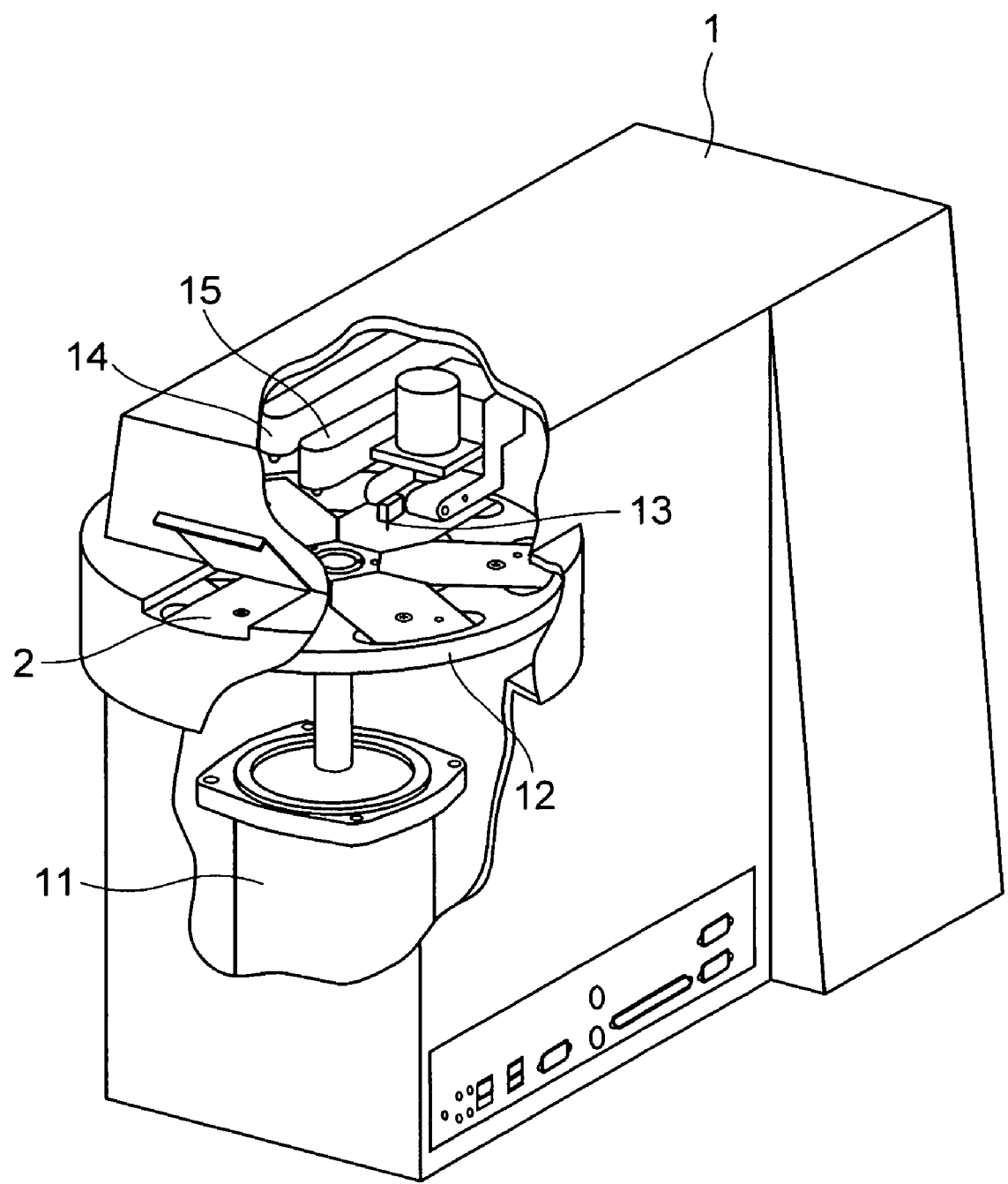
FIG. 1 is a perspective view showing an outward appearance of a chemical analysis apparatus according to the invention.

FIG. 1 is a view showing an example of a chemical analysis apparatus according to the invention. The chemical analysis apparatus 1 comprises a motor 11, a holding disk 12 that can be rotated by the motor 11, a plurality of examination cartridges 2 arranged on the holding disk 12, a perforator 13 that forms a hole on the examination cartridges 2, a heating device 14, and a detection device 15. An operator prepares examination cartridges 2 every item of detection to mount the same on the holding disk 12 and starts the chemical analysis apparatus 1.

With the chemical analysis apparatus of this example, the heating device 14 and the detection device 15, respectively, are provided in separate locations but the both may be made, for example, integral with each other and heating and detection may be performed in the same position. Also, while the heating device and the detection device are arranged on an upper surface of the holding disk 12, either of, or both of them may be arranged on an underside of the holding disk 12.

Figure 2:
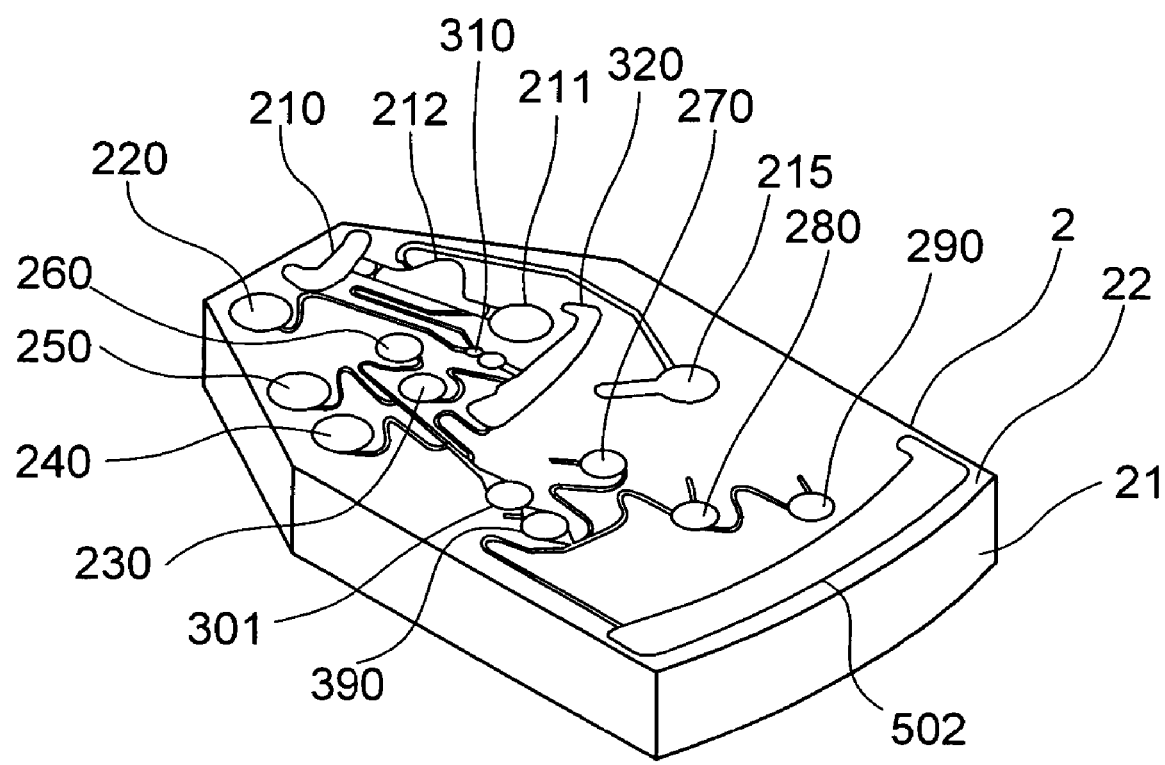
FIG. 2 is a perspective view showing an outward appearance of an examination cartridge according to the invention.

FIG. 2 is a perspective view showing the examination cartridge 2. The examination cartridge 2 comprises a thin substrate 21 having a substantially hexagonal shape, and a cartridge cover 22 made of film, thin sheet, or the like is bonded or joined to the upper surface of the examination cartridge 2 so as to cover the whole of the cartridge upper surface. Accordingly, the vessels and the flow channels define closed spaces. A short side of the hexagonal shape is arranged on an inner peripheral side of the holding disk about a center of rotation and a long side of the hexagonal shape is arranged on an outer peripheral side. Accordingly, the side of the short side of the hexagonal shape is referred below to as an inner peripheral side and the side of the long side of the hexagonal shape is referred below to as an outer peripheral side.

The examination cartridge 2 is formed with a lysis reagent vessel 220, an additional-liquid vessel 230, washing-liquid vessels 240, 250, 270, an eluant vessel 260, and detection reagent vessels 280, 290. Reagents are beforehand dispensed to these reagent vessels by predetermined amounts.

The examination cartridge 2 is further provided with a specimen vessel 210, a hemocyte storage vessel 211, a serum quantitative vessel 212, a whole blood waste vessel 215, a nucleic-acid trap part 301, a mixing vessel 310, a reaction vessel 320, an eluant recovery vessel 390, and a waste-liquid storage vessel 502. The nucleic-acid trap part 301 includes a porous material of quartz or glass, fiber filter, etc. These vessels are interconnected by means of flow channels. These vessels and these flow channels comprise recesses formed on an upper surface of the examination cartridge 2. The flow channels are smaller in depth than the vessels.

In this example, a centrifugal force is made use of to move a reagent or a solution between two vessels interconnected by a flow channel. First, the cartridge cover 22 covering two vessels is perforated to open two vessels to the atmosphere. Subsequently, the holding disk 12 is rotated to cause the action of a centrifugal force to move a reagent or a solution in the vessel from the vessel on the inner peripheral side to the vessel on the outer peripheral side. Such operation is successively repeated to enable executing a predetermined process.

Figure 3:
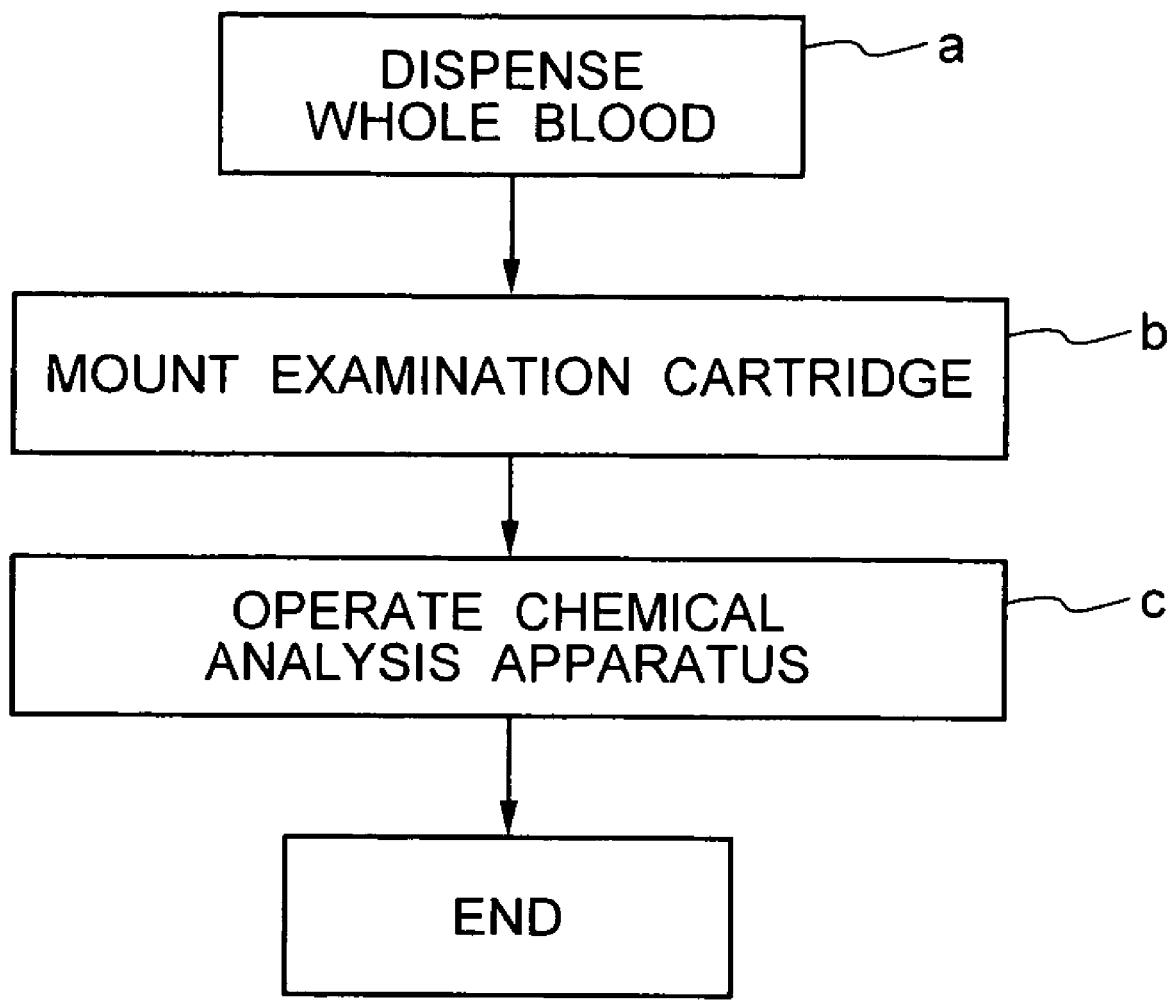
FIG. 3 is a view illustrating an outline of an operating procedure in the case where the chemical analysis apparatus according to the invention is used to perform a process of extracting a viral nucleic acid from whole blood.

Operations of extraction and analysis of a viral nucleic acid in the case where whole blood is used as a specimen will be described hereinafter. As shown in FIG. 3, in STEP a, an operator dispenses whole blood, which is drawn by a vacuum blood-collection tube, etc., to the examination cartridge 2. In STEP b, a necessary number of the examination cartridges 2 are mounted on the holding disk 12 shown in FIG. 1. In STEP c, the chemical analysis apparatus 1 is operated. Thereby, a viral nucleic acids are extracted from whole blood and the nucleic acids are detected, finally.

Figure 4:
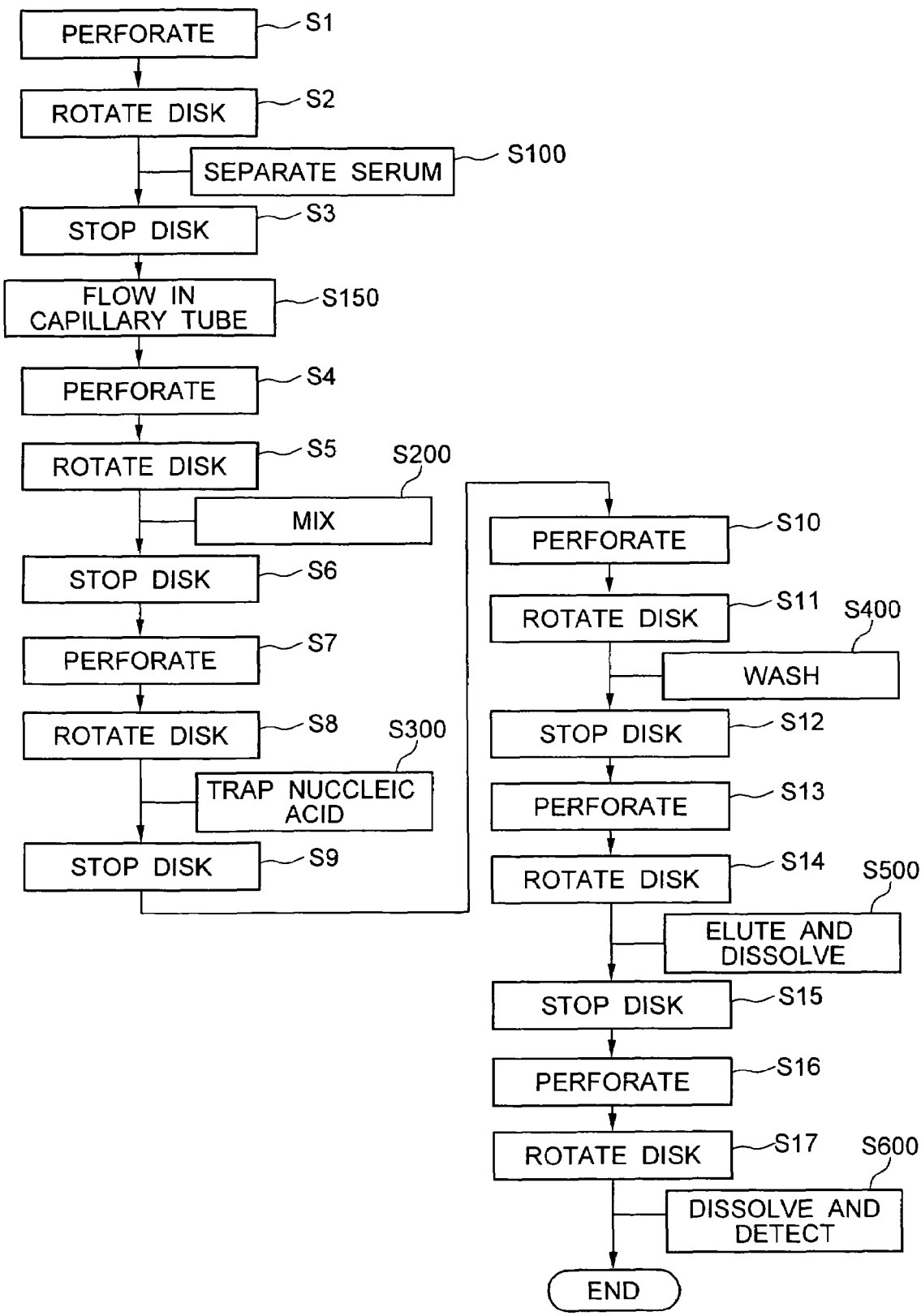
FIG. 4 is a view illustrating the operating procedure in the case where the chemical analysis apparatus according to the invention is used to perform the process of extracting a viral nucleic acid from whole blood.
Figure 5:
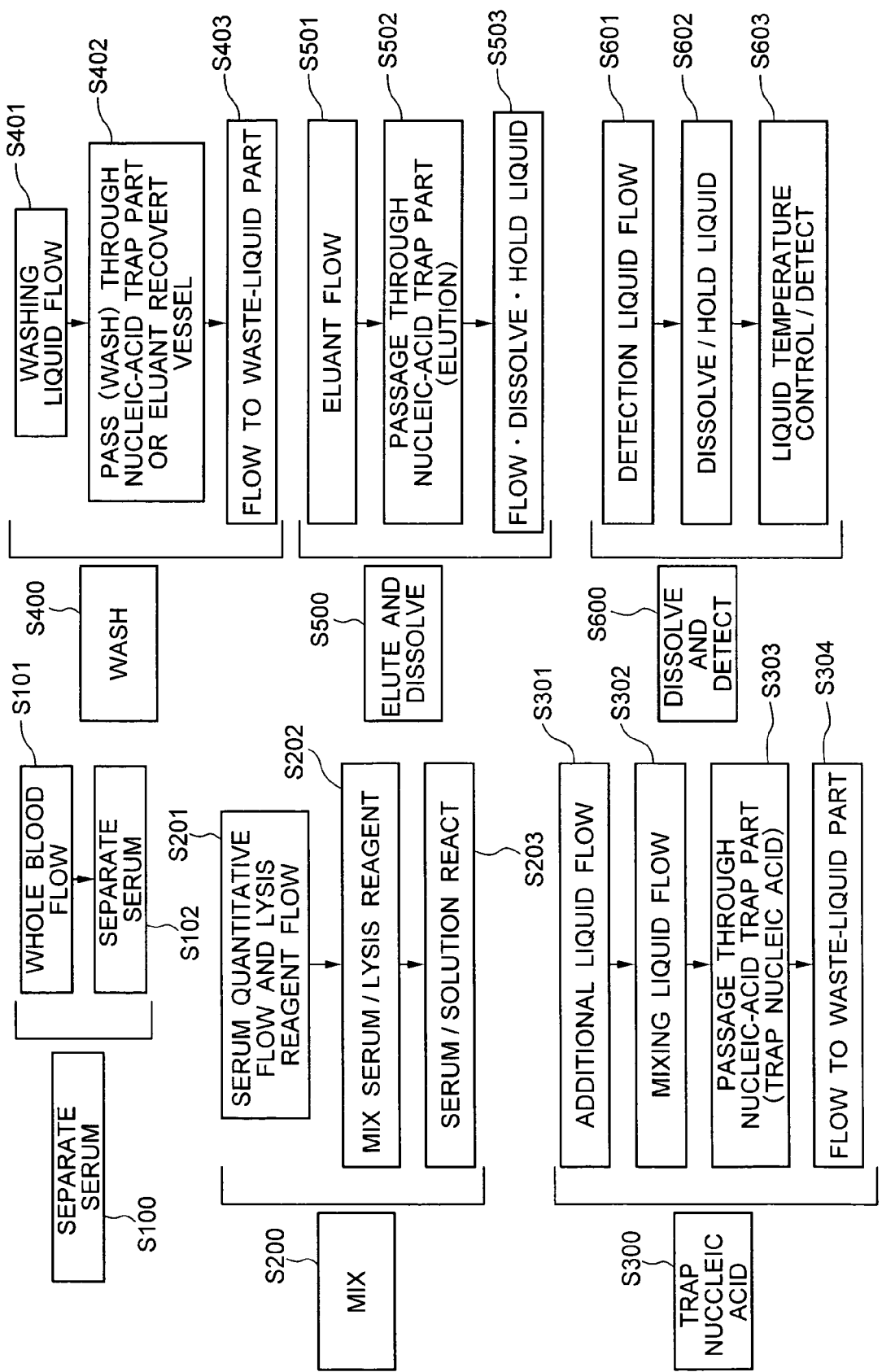
FIG. 5 is a view illustrating details of the procedure in the case where the chemical analysis apparatus according to the invention is used to perform the processing of extracting a viral nucleic acid from whole blood.

FIG. 4 shows an outline of operations of the chemical analysis apparatus. FIG. 5 shows contents of the respective operations. In STEP S1, the cartridge cover 22 is perforated to connect the specimen vessel 210, the serum quantitative vessel 212, the hemocyte storage vessel 211, and the whole blood waste vessel 215 to the atmosphere. In STEP S2, the holding disk 12 is rotated. Thereby, in STEP S100, serum in the whole blood is separated from hemocyte. Serum separation in STEP S100 includes two processes as shown in FIG. 5. In flow of the whole blood in STEP S101, the whole blood in the specimen vessel 210 moves to the serum quantitative vessel 212 and the hemocyte storage vessel 211. In serum separation in STEP S102, serum and hemocyte, respectively, are separated into the serum quantitative vessel 212 and the hemocyte storage vessel 211. In STEP S3, rotation of the holding disk 12 is stopped. In STEP S150, a part of serum in the serum quantitative vessel 212 is moved in a serum capillary tube by a capillary tube force due to surface tension.

In STEP S4, the cartridge cover 22 is perforated to connect the lysis reagent vessel 220 and the reaction vessel 320 to the atmosphere. In STEP S5, the holding disk 12 is rotated. Thereby, in STEP S200, serum and a solution are mixed in the reaction vessel 320. Mixing in STEP S200 includes three processes as shown in FIG. 5. In serum quantitative flow and lysis reagent flow in STEP S201, the lysis reagent in the lysis reagent vessel 220 and the serum in the serum quantitative vessel 212 move to the reaction vessel 320. In mixing of the serum and the lysis reagent in STEP S202, the serum and the lysis reagent are mixed. In STEP S203, the serum and the solution react with each other. In STEP S6, rotation of the holding disk 12 is stopped.

In STEP S7, the cartridge cover 22 is perforated to connect the additional-liquid vessel 230, the eluant recovery vessel 390, and the waste-liquid storage vessel 502 to the atmosphere. In STEP S8, the holding disk 12 is rotated. Thereby, in STEP S300, nucleic acids are trapped. Trapping of the nucleic acid in STEP S300 includes four processes as shown in FIG. 5. In flow of an additional liquid in STEP S301, the additional liquid in the additional-liquid vessel 230 moves to the reaction vessel 320. In flow of a mixing liquid in STEP S302, the mixing liquid in the additional-liquid vessel 230 is pushed out by the additional liquid to move to the nucleic-acid trap part

301. In passage through the nucleic-acid trap part in STEP S303, the mixing liquid passes through the nucleic-acid trap part. In STEP S304, the mixing liquid having passed through the nucleic-acid trap part moves to the waste-liquid storage vessel 502 through the eluant recovery vessel 390. In STEP S9, rotation of the holding disk 12 is stopped.

Subsequently, a washing process will be described. The washing process includes first, second, and third washing processes. Operations in STEP S10 to STEP S12 and STEP S400 are repeated for all the washing processes. First, the first washing process is described. In STEP S10, the cartridge cover 22 is perforated to connect the first washing-liquid vessel 240 to the atmosphere. In STEP S11, the holding disk 12 is rotated. Thereby, in STEP S400, washing is performed. Washing in STEP S400 includes three processes as shown in FIG. 5. In flow of a washing liquid in STEP S401, the washing liquid in the first washing-liquid vessel 240 moves to the nucleic-acid trap part 301. In STEP S402, the washing liquid in the first washing-liquid vessel 240 washes the nucleic-acid trap part 301. In STEP S403, the washing liquid, which has washed the nucleic-acid trap part 301, moves to the waste-liquid storage vessel 502. In STEP S12, rotation of the holding disk 12 is stopped.

Subsequently, the second washing process will be described. In STEP S10, the cartridge cover 22 is perforated to connect the second washing-liquid vessel 250 to the atmosphere. The subsequent processing is the same as that in the first washing process. The third washing process will be described. In STEP S10, the cartridge cover 22 is perforated to connect the third washing-liquid vessel 270 to the atmosphere. In STEP S11, the holding disk 12 is rotated. Thereby, in STEP S400, washing is performed. In flow of a washing liquid in STEP S401, the washing liquid in the third washing-liquid vessel 270 moves to the eluant recovery vessel 390. In STEP S402, the washing liquid in the third washing-liquid vessel 270 washes the eluant recovery vessel 390. In STEP S403, the washing liquid, which has washed the eluant recovery vessel 390, moves to the waste-liquid storage vessel 502. In STEP S12, rotation of the holding disk 12 is stopped.

In STEP S13, the cartridge cover 22 is perforated to connect the eluant vessel 260 and the first detection reagent vessel 280 to the atmosphere. In STEP S14, the holding disk 12 is rotated. Thereby, in STEP S500, elution and dissolution are performed. Elution and dissolution in STEP S500 include three processes as shown in FIG. 5. In flow of an eluant in STEP S501, the eluant in the eluant vessel 260 moves to the nucleic-acid trap part 301. In STEP S502, the eluant passes through the nucleic-acid trap part 301 to elute nucleic acids trapped by the nucleic-acid trap part 301. In STEP S503, the eluant, which has eluted nucleic acids, moves to the first detection reagent vessel 280 to dissolve a dry first examination reagent. In STEP S15, rotation of the holding disk 12 is stopped.

In STEP S16, the cartridge cover 22 is perforated to connect the second detection reagent vessel 290 to the atmosphere. In STEP S17, the holding disk 12 is rotated. Thereby, in STEP S600, dissolution and detection are performed. Dissolution and detection in STEP S600 include three processes as shown in FIG. 5. In flow of a detection liquid in STEP S600, a solution in the first detection reagent vessel 280 moves to the second detection reagent vessel 290. In STEP S602, a second detection reagent in the second detection reagent vessel 290 dissolves and is held. In STEP S603, the second detection reagent vessel 290 is heated. A nucleic acid in the second detection reagent vessel 290 is examined by an examination apparatus.

Operations of the chemical analysis apparatus will be described hereinafter in detail.

Figure 6:
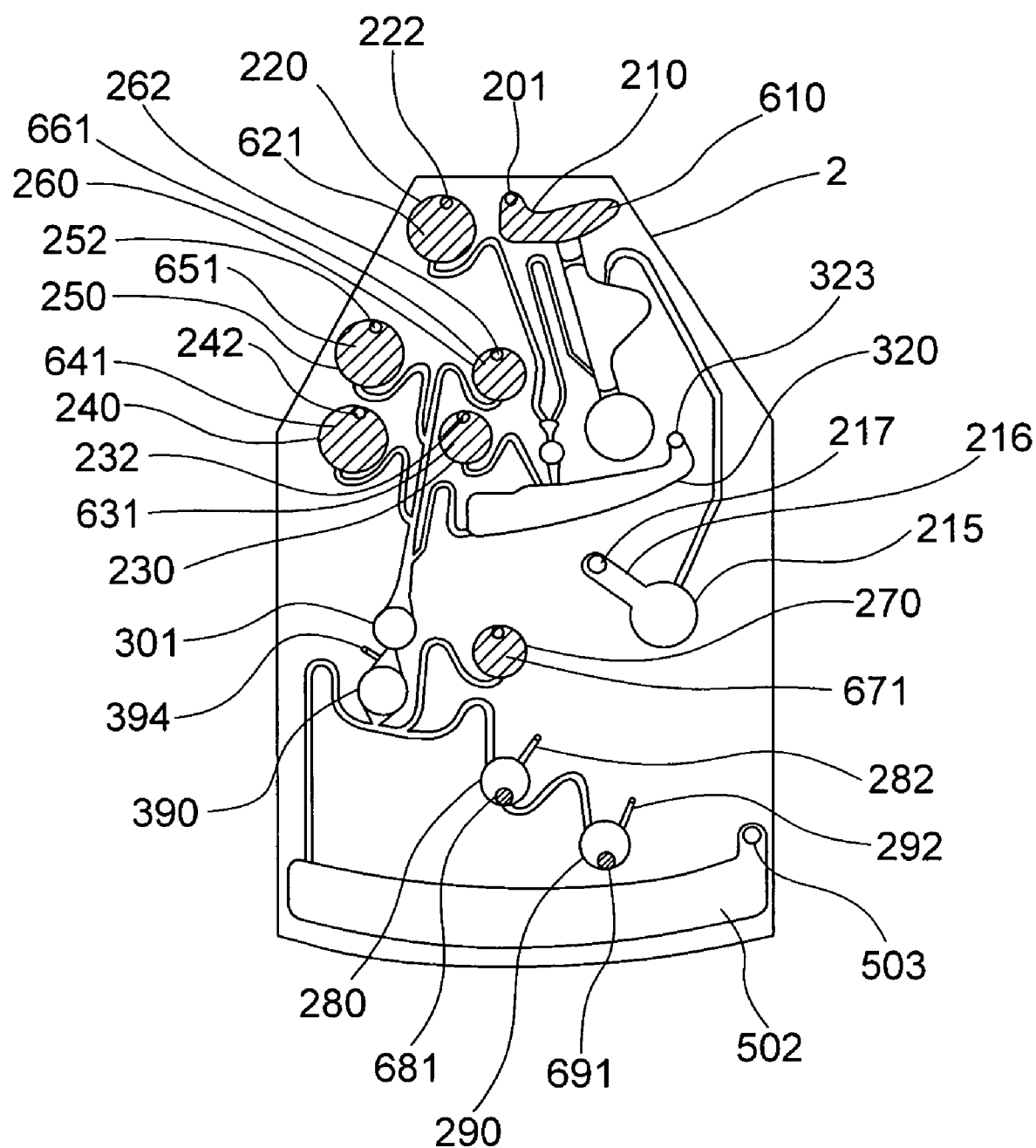
FIG. 6 is a view illustrating an operation of the examination cartridge according to the invention.

An explanation will be given below with reference to FIG. 6. A lysis reagent 621 for lysing of viral membrane protein in the serum to elute nucleic acids is dispensed to the solution vessel 220. The lysis reagent 621 dissolves protein, which forms membrane of virus and bacteria in the serum, and promotes adsorption of the nucleic acid to the nucleic-acid trap part 301. The lysis reagent 621 may be guanidine hydrochloride, for example, for lysing and adsorption of DNA and guanidine thiocyanate for lysing and adsorption of RNA.

An additional liquid 631 for replenishment of the lysis reagent is dispensed to the additional-liquid vessel 230. The additional liquid 631 may be, for example, the lysis reagent 621 itself. A first washing liquid 641 for washing of unnecessary components, such as protein, etc., adhered to the nucleic-acid trap part 301 is dispensed to the first washing-liquid vessel 240. The first washing liquid 641 may be, for example, the lysis reagent 621 or a liquid obtained by reducing the lysis reagent 621 in salt level. A second washing liquid 651 for washing of unnecessary components, such as salt, etc., adhered to the nucleic-acid trap part 301 is dispensed to the second washing-liquid vessel 250. The second washing liquid 651 may be, for example, ethanol or an ethanol water solution. An eluant 661 for elution of nucleic acids from the nucleic-acid trap part 301 is dispensed to the eluant vessel 260. The eluant 661 may be sterilized water, or a water solution adjusted to 7 to 9 in pH.

A third washing liquid 671 for washing of components, such as etahnol, etc., adhered to the eluant recovery vessel 390 is dispensed to the third washing-liquid vessel 270. The third washing liquid 671 may be, for example, sterilized water, or a water solution adjusted to 7 to 9 in pH.

A dry first detection reagent 681 and a dry second detection reagent 691, respectively, in a dry state are preserved in the first detection reagent vessel 280 and the second detection reagent vessel 290. The dry first detection reagent may be, for example, primer, probe, deoxynucleoside triphosphate, and the dry second detection reagent may be enzyme. All reagent components contained in the two detection reagents may be preserved as one kind of dry detection reagent in the second detection reagent vessel 290. In this case, the first detection reagent vessel 280 can be omitted.

The detection reagents are preserved in a dry state whereby they can be preserved at room temperature or in cold storage over a long term. In the case where preservation in a dry state is unnecessary, however, it suffices to beforehand solve the detection reagents in the eluant 661.

Vent holes 222, 232, 242, 252, 262, 272, 282, 292 are respectively provided on inner peripheral ends of the reagent vessels 220, 230, 240, 250, 260, 270, 280, 290. A vent hole 217 is provided on an inner peripheral end of the whole blood waste vessel 215 with an air flow channel 216 therebetween. Vent holes 323, 394, 503 are respectively provided on inner peripheral ends of the reaction vessel 320, the eluant recovery vessel 390, and the waste-liquid storage vessel 502. These vessels are connected to the atmosphere by perforating the cover above these vent holes.

The specimen vessel 210 is provided with a specimen injection port 201. An operator perforates the cartridge cover 22 above the specimen injection port 201 of the examination cartridge 2 and injects whole blood 610, which is drawn by a vacuum blood-collection tube, etc., into the specimen vessel 210 through the specimen injection port 201.

First, a serum separating processing in STEP S100 is described. The perforator 13 is used to perforate the cover above the vent hole 217 of the whole blood waste vessel.

Thereby, the whole blood waste vessel 215 is connected to the atmosphere through the vent hole 217. In addition, the specimen vessel 210 is connected to the atmosphere through the specimen injection port 201.

Figure 7:
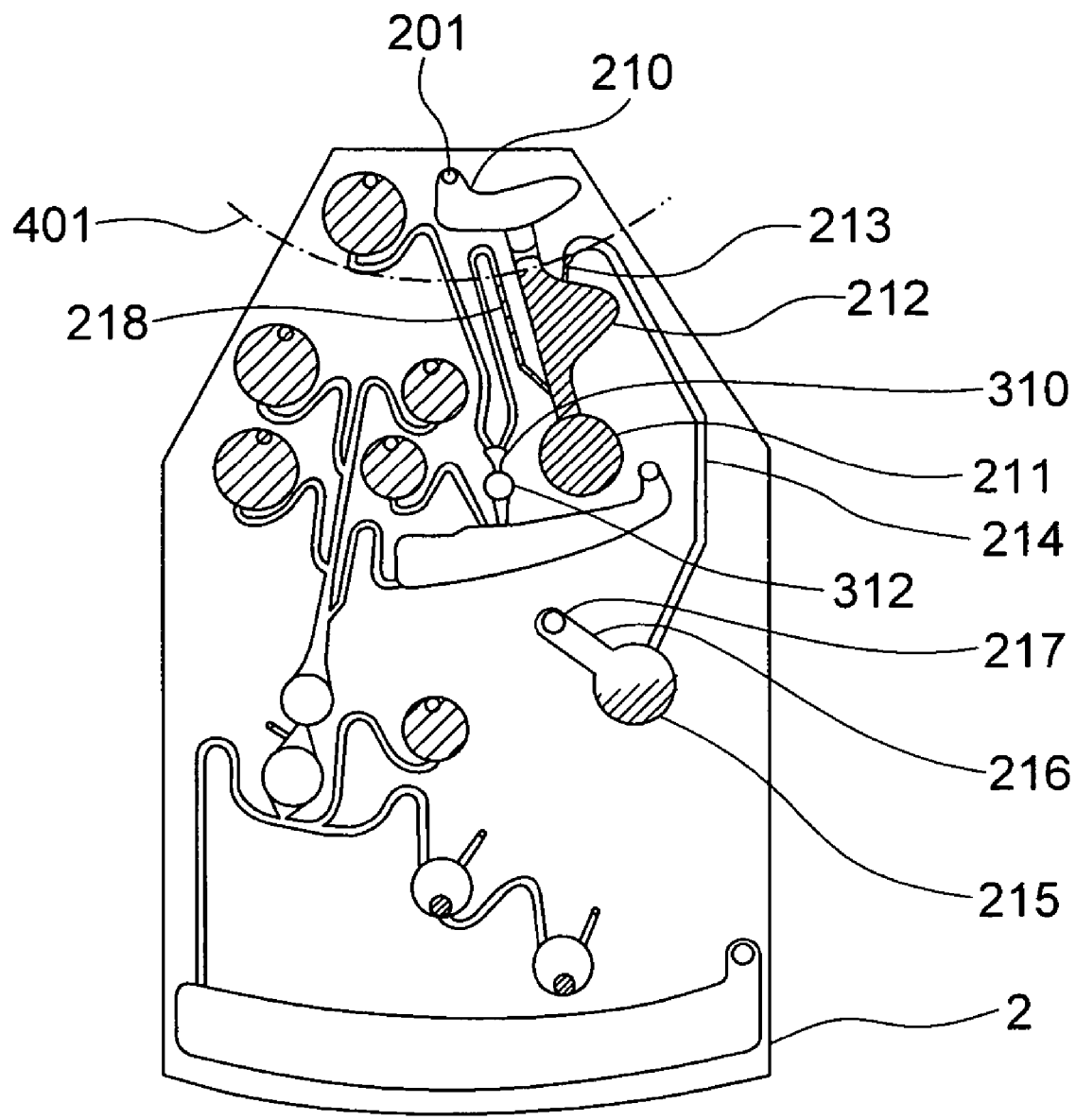
FIG. 7 is a view illustrating an operation of the examination cartridge according to the invention.

The motor 11 is actuated to rotate the holding disk 12. As shown in FIG. 7, the whole blood in the specimen vessel 210 is caused by the action of a centrifugal force to move toward the outer peripheral side to flow into the hemocyte storage vessel 211 and the serum quantitative vessel 212.

Provided between the serum quantitative vessel 212 and the whole blood waste vessel 215 is an overflow flow channel having a return portion starting from an inner peripheral end of the serum quantitative vessel 212, extending toward the inner peripheral side, and again extending toward the outer peripheral side. The overflow flow channel includes a narrow overflow channel 213, which is small in cross sectional area from the serum quantitative vessel 212 to the return portion, and a wide overflow channel 214, which is large in cross sectional area from the return portion to the whole blood waste vessel 215. That is, the narrow overflow channel 213 and the wide overflow channel 214 are connected to each other at the return portion. Accordingly, when the hemocyte storage vessel 211 and the serum quantitative vessel 212 are filled with whole blood, the whole blood flows to the whole blood waste vessel 215 through the overflow flow channel.

When rotation of the holding disk 12 is continued, hemocyte 612 moves to the hemocyte storage vessel 211 on the outer peripheral side and serum 613 remains in the serum quantitative vessel 212 on the inner peripheral side. That is, the whole blood 610 is separated into hemocyte and serum. When rotation is continued for a predetermined period of time and the serum centrifugal separating operation is terminated, rotation of the holding disk 12 is stopped.

Figure 8:
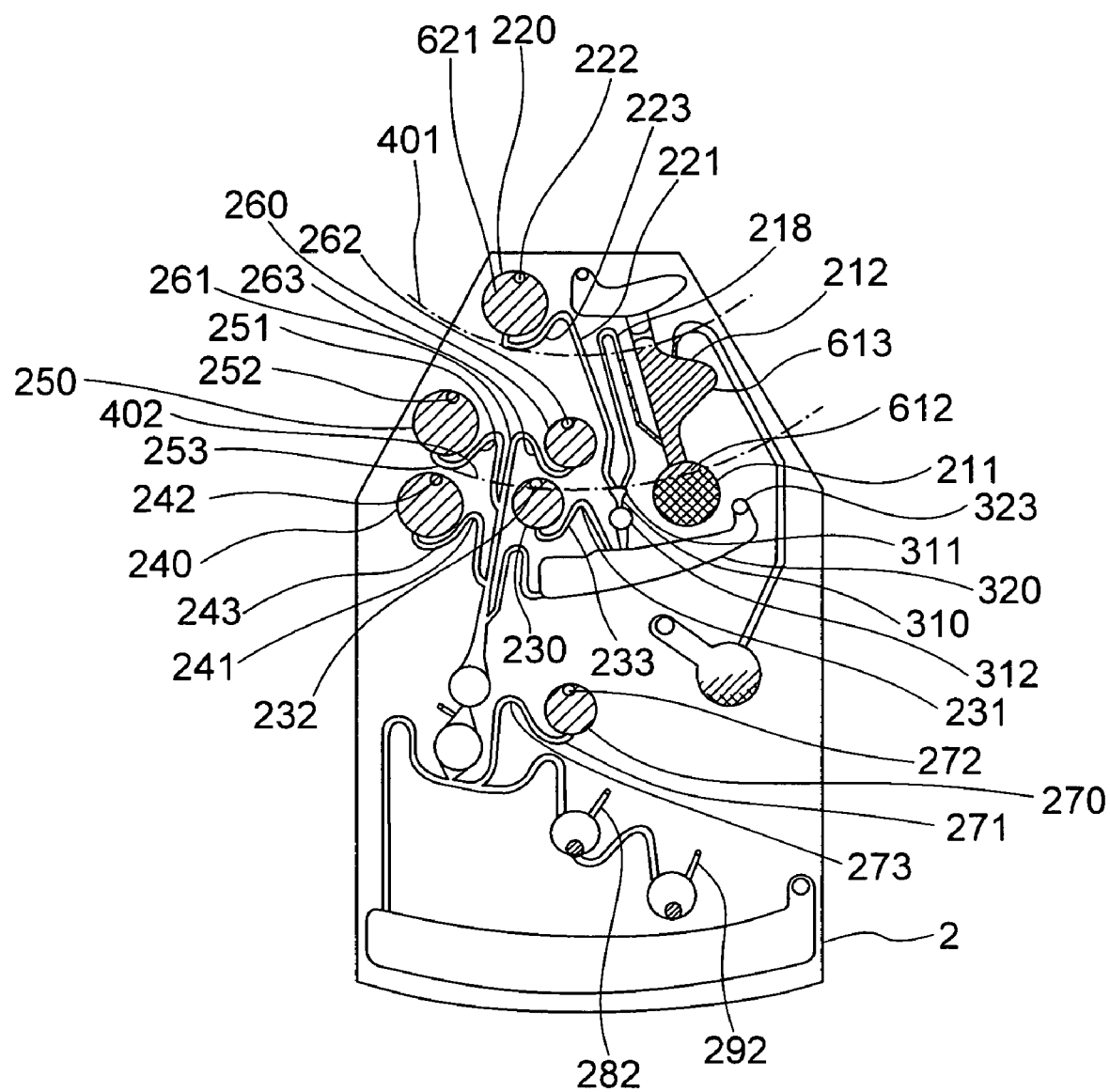
FIG. 8 is a view illustrating an operation of the examination cartridge according to the invention.

FIG. 8 shows a state, in which the whole blood 610 is separated into hemocyte and serum, the hemocyte 612 moves to the hemocyte storage vessel 211 on the outer peripheral side, and the serum 613 remains in the serum quantitative vessel 212 on the inner peripheral side. A weir is provided between the serum quantitative vessel 212 and the hemocyte storage vessel 211, so that the hemocyte 612 in the hemocyte storage vessel 211 cannot return into the serum quantitative vessel 212.

Flow in the serum capillary tube in STEP S150 will be described. Provided between the serum quantitative vessel 212 and the mixing vessel 310 is a serum capillary tube 218 having a return portion starting from an inner peripheral end of the serum quantitative vessel 212, extending toward the inner peripheral side, and again extending toward the outer peripheral side. A part of the serum 613 in the serum quantitative vessel 212 is moved in the serum capillary tube 218 by a capillary tube force due to surface tension to reach the mixing vessel inlet 311 at a boundary of the mixing vessel 310 and the serum capillary tube 218. Since the mixing vessel 310 is enlarged in cross sectional area, however, the capillary tube force decreases, so that the serum is not moved further. Likewise, while a part of the serum 613 in the serum quantitative vessel 212 is moved in the narrow overflow channel 213 by a capillary tube force due to surface tension, the wide overflow channel 214 is enlarged in cross sectional area, so that the capillary tube force decreases and the serum is not moved further. A radial position 401 indicates liquid level in the serum quantitative vessel 212 and the narrow overflow channel 213.

In this example, the serum quantitative vessel 212 has function of quantitating a predetermined amount of serum. For example, let assume that the hemocyte storage vessel 211 has a volume of 250 microliter and a necessary amount of serum is 200 microliter. When whole blood of 500 microliter is dispensed to the specimen vessel 210, whole blood of 50 microliter overflows to the whole blood waste vessel 215 and the remaining whole blood of 450 microliter is separated into hemocyte and serum. Serum of 200 microliter out of the separated serum flows out to the mixing vessel 310. In the example, serum of 200 microliter or more can be obtained from whole blood of 450 microliter. In case of whole blood having a small ratio of serum, it suffices that a hemocyte storage vessel be increased in volume and a whole blood specimen be increased.

Outlet flow channels 221, 231, 241, 251, 261, 271 are provided on outer peripheral sides of the reagent vessels 220, 230, 240, 250, 260; 270. Formed on the outlet flow channels are return portions 223, 233, 243, 253, 263, 273 starting from outer peripheral ends of the reagent vessels, and returning toward the inner peripheral side.

Since the cartridge cover 22 is mounted to the upper surface of the substrate 21, the reagent vessels 220, 230, 240, 250, 260, 270 and the outlet flow channels 221, 231, 241, 251, 261, 271 are closed to allow no air to flow thereinto unless the cartridge cover 22 is perforated in positions, which correspond to the vent holes. However, a very small amount of an air charged when the cartridge cover is mounted is present in the reagent vessels and the outlet flow channels. When a centrifugal force acts, respective reagents move to the outer peripheral sides of the reagent vessels to be pushed into the outlet flow channels but a very small amount of an air initially charged into the reagent vessels expands to generate negative pressures in the reagent vessels. The negative pressure and the centrifugal force balance each other out and so the reagents cannot flow out of the reagent vessels.

When a rotating speed increases and a centrifugal force increases, pressures in the reagent vessels further drop to become equal to or lower than saturation vapor pressures of the reagents, at which bubbles are generated. Thereby, the pressures increase and the balance to the centrifugal force is broken. In the example, since return portions 223, 233, 243, 253, 263, 273 returning toward the inner peripheral side are provided on the outlet flow channels 221, 231, 241, 251, 261, 271 of the respective reagent vessels, however, a decrease in pressure in the reagent vessels is restricted and the reagents are prevented from flowing out of the outlet flow channels even when the centrifugal force increases.

The perforator 13 is used to perforate the cartridge cover 22 in positions, which correspond to the vent holes of the respective reagent vessels, to connect the respective reagent vessels to the atmosphere. The motor 11 rotates the holding disk whereby a centrifugal force causes respective reagents to flow.

The mixing processing in STEP S200 will be described. The perforator 13 is used to perforate the cartridge cover 22 in that position, which corresponds to the vent hole 222 of the lysis reagent vessel 220. The cartridge cover 22 is perforated in that position, which corresponds to the vent hole 323 of the reaction vessel 320. Thereby, the lysis reagent vessel 220 and the reaction vessel 320 are connected to the atmosphere.

Figure 9:
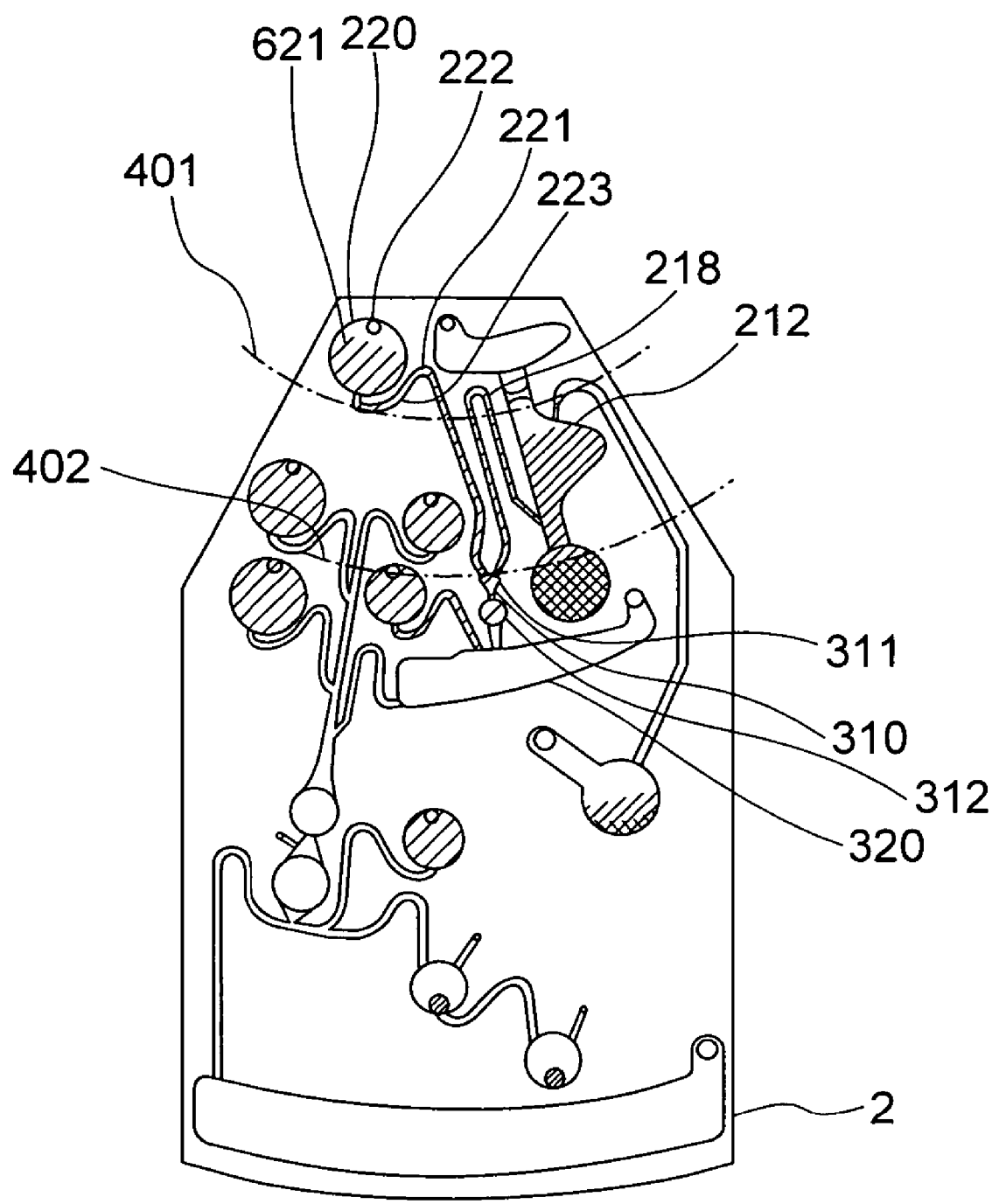
FIG. 9 is a view illustrating an operation of the examination cartridge according to the invention.

The motor 11 is actuated to rotate the holding disk 12. As shown in FIG. 9, the lysis reagent 621 in the lysis reagent vessel 220 is caused by the action of a centrifugal force to flow toward the outer peripheral side to move to the reaction vessel 320 through the lysis reagent vessel outlet flow channel 221 having the return portion, the mixing vessel 310, and a flow channel enlarged portion 312.

The serum 613 in the serum quantitative vessel 212 is caused by the action of a centrifugal force to flow toward the outer peripheral side to move to the reactive vessel 320 through the serum capillary tube 218, the mixing vessel 310, and a flow channel enlarged portion 312.

Figure 10:
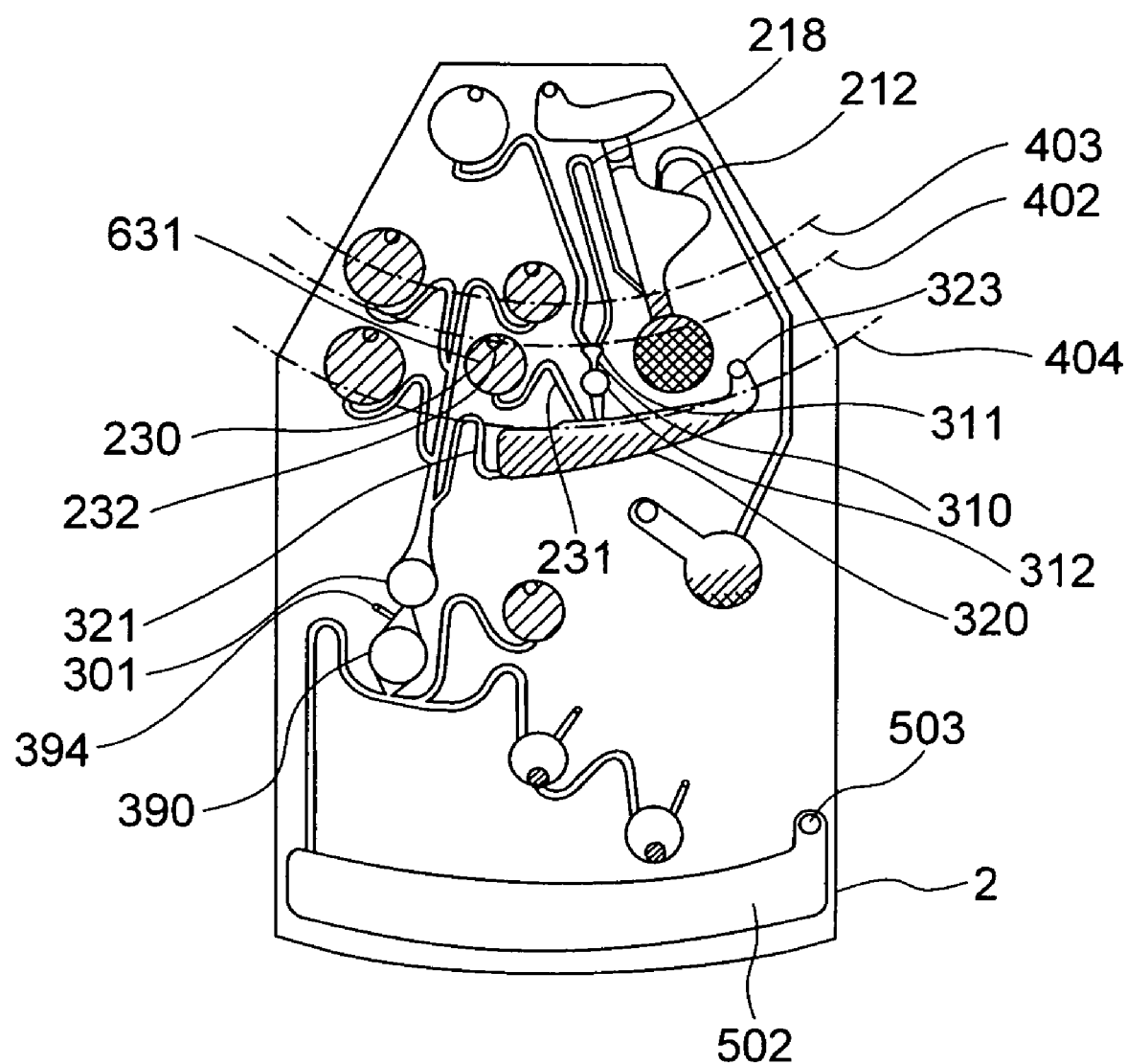
FIG. 10 is a view illustrating an operation of the examination cartridge according to the invention.

As shown in FIG. 10, a radial position 401 at the outlet of the lysis reagent vessel 220 is nearer to the inner peripheral side than a radial position 402 at the mixing vessel inlet 311, and therefore, all the lysis reagent 621 in the lysis reagent vessel 220 flows out into the mixing vessel 310 owing to siphon action.

A radial position 403 passing through a position, in which the serum quantitative vessel 212 and the serum capillary tube 218 are connected to each other, is nearer to the inner peripheral side than the radial position 402 at the mixing vessel inlet 311. Accordingly, all serum present toward the inner peripheral side from the radial position 403, out of serum in the serum quantitative vessel 212 flows out into the mixing vessel 310 owing to the siphon action. The lysis reagent and the serum, which have flowed into the mixing vessel 310, move to the reaction vessel 320 through the flow channel enlarged portion 312. The serum and the lysis reagent 621 are mixed in the reaction vessel 320 to react with each other.

While the reaction vessel 320 serves as a space, in which a solution and serum are mixed together, a member to accelerate mixing of serum and a solution may be provided therein. The member for acceleration of mixing includes a porous filter made of resin, glass, paper, etc., or fiber, a projection of silicone, metal, etc., manufactured by etching, machining, or the like.

Provided between the reaction vessel 320 and the nucleic-acid trap part 301 is a reaction vessel outlet flow channel 321 having a return portion starting from an outer peripheral end of the reaction vessel 320, and extending toward the inner peripheral side. During rotation, liquid level in the reaction vessel 320 is positioned toward the outer peripheral side from a radial position 404 at an innermost peripheral end of the return portion of the reaction vessel outlet flow channel 321. Accordingly, a mixing liquid in the reaction vessel 320 is not moved toward the nucleic-acid trap part 301 beyond the return portion of the reaction vessel outlet flow channel 321. During rotation, the mixing liquid is held in the reaction vessel 320.

When rotated for a predetermined period of time to terminate the mixing process of serum and the lysis reagent, the motor 11 is stopped to stop rotation of the holding disk 12.

Subsequently, an explanation will be given to the nucleic-acid trapping processing in STEP S300. As shown in FIG. 10, provided between the additional-liquid vessel 230 and the reaction vessel 320 is the additional-liquid vessel outlet flow channel 231 having a return portion starting from an outer peripheral end of the additional-liquid vessel 230, and extending toward the inner peripheral side.

The perforator 13 is used to perforate the cartridge cover 22 in that position, which corresponds to the vent hole 232 of the additional-liquid vessel 230, to connect the additional-liquid vessel 230 to the atmosphere. The perforator 13 is used to perforate the cartridge cover 22 in that position, which corresponds to the vent hole 394 of the eluant recovery vessel 390, to connect the eluant recovery vessel 390 to the atmosphere. The perforator 13 is used to perforate the cartridge cover 22 in that position, which corresponds to the vent hole 503 of the waste-liquid storage vessel 502, to connect the waste-liquid storage vessel 502 to the atmosphere.

Figure 11:
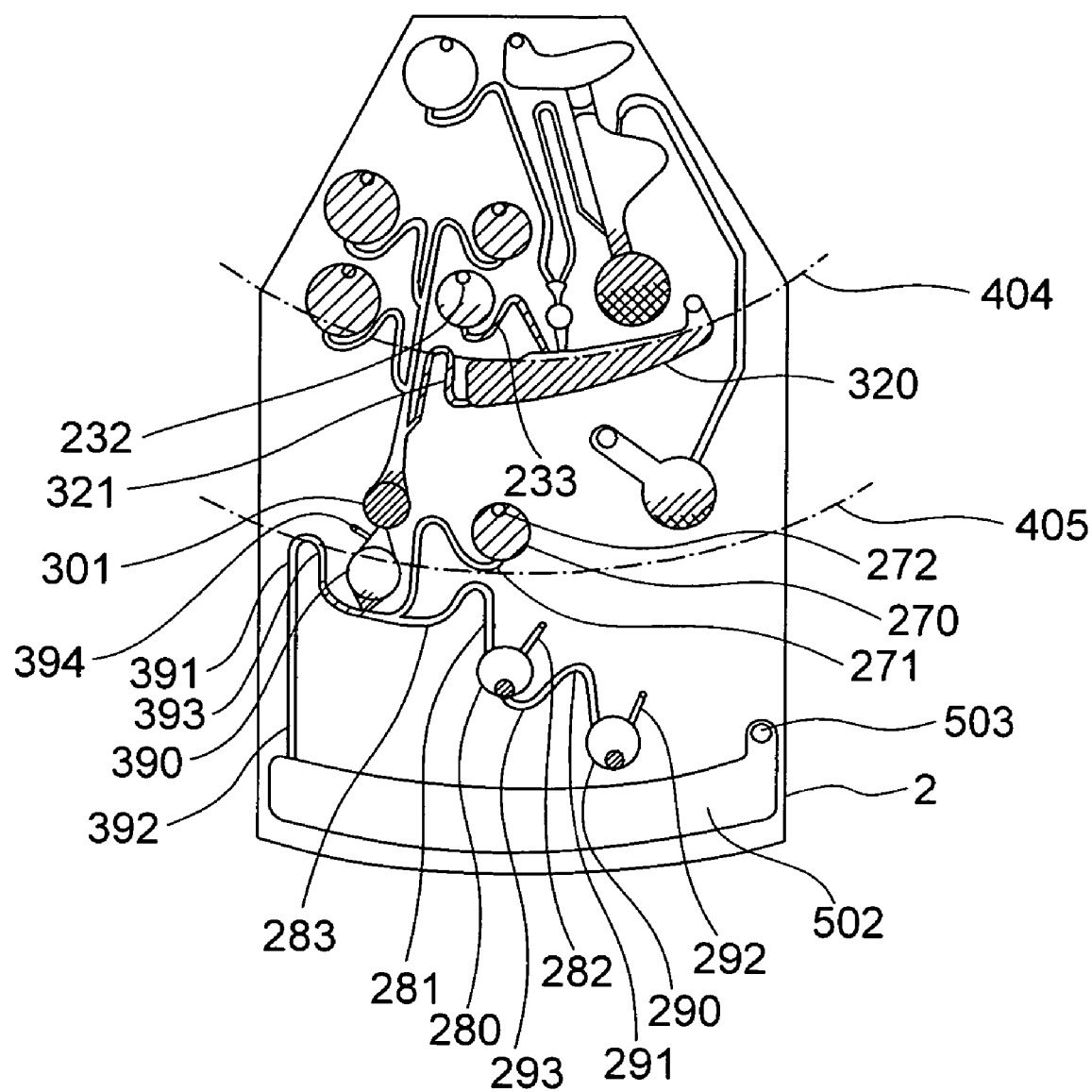
FIG. 11 is a view illustrating an operation of the examination cartridge according to the invention.

The motor 11 is actuated to rotate the holding disk 12. The solution 631 in the additional-liquid vessel 230 is caused by the action of a centrifugal force to move to the reaction vessel 320 through the additional-liquid vessel outlet flow channel 231. Thereby, a liquid level of a mixing liquid in the reaction vessel 320 is moved toward the inner peripheral side. As shown in FIG. 11, when the liquid level of the mixing liquid reaches a position 404 at an innermost periphery of the reaction vessel outlet flow channel 321, the mixing liquid flows over the return portion of the reaction vessel outlet flow channel 321 to flow into the nucleic-acid trap part 301.

When a mixing liquid of serum and the lysis reagent has a good wettability to a wall surface, the mixing liquid flows back sometimes moves in the reaction vessel outlet flow channel 321 due to the capillary phenomenon. In such case, the additional liquid 631 is not needed.

The mixing liquid having been led to the nucleic-acid trap part 301 moves toward the outer peripheral side due to the action of the centrifugal force to pass through the nucleic-acid trap part 301. When the mixing liquid passes through the nucleic-acid trap part, nucleic acids in the mixing liquid are adsorbed by the nucleic-acid trap part 301 and the remaining waste liquid flows into the eluant recovery vessel 390.

Provided between the eluant recovery vessel 390 and the waste-liquid storage vessel 502 is an eluant recovery vessel outlet flow channel 391 having a return portion 393 starting from an outer peripheral end of the eluant recovery vessel 390, and extending toward the inner peripheral side. Provided between the third washing-liquid vessel 270 and the eluant recovery vessel outlet flow channel 391 is a third washing-liquid vessel flow channel 271 having a return portion starting from an outer peripheral end of the third washing-liquid vessel 270, and extending toward the inner peripheral side.

Provided between the eluant recovery vessel 390 and the first detection reagent vessel 280 is a first detection liquid inflow channel 281 having a return portion 283 starting from an outer peripheral end of the eluant recovery vessel 390, and extending toward the inner peripheral side. Provided between the first detection reagent vessel 280 and the second detection reagent vessel 290 is a second detection liquid inflow channel 291 having a return portion 293 starting from an outer peripheral end of the first detection reagent vessel 280, and extending toward the inner peripheral side.

While the eluant recovery vessel 390 and the waste-liquid storage vessel 502 are connected to the atmosphere, the third washing-liquid vessel 270, the first detection reagent vessel 280, and the second detection reagent vessel 290 are not connected to the atmosphere.

The eluant recovery vessel 390 is smaller in volume than the mixing liquid in the reaction vessel 320. Accordingly, a waste liquid, which has flowed into the eluant recovery vessel 390, flows into the eluant recovery vessel outlet flow channel 391 to flow to the waste-liquid storage vessel 502 over the return portion 393. When all the waste liquid moves to the waste-liquid storage vessel 502, the next washing process is executed.

Figure 12:
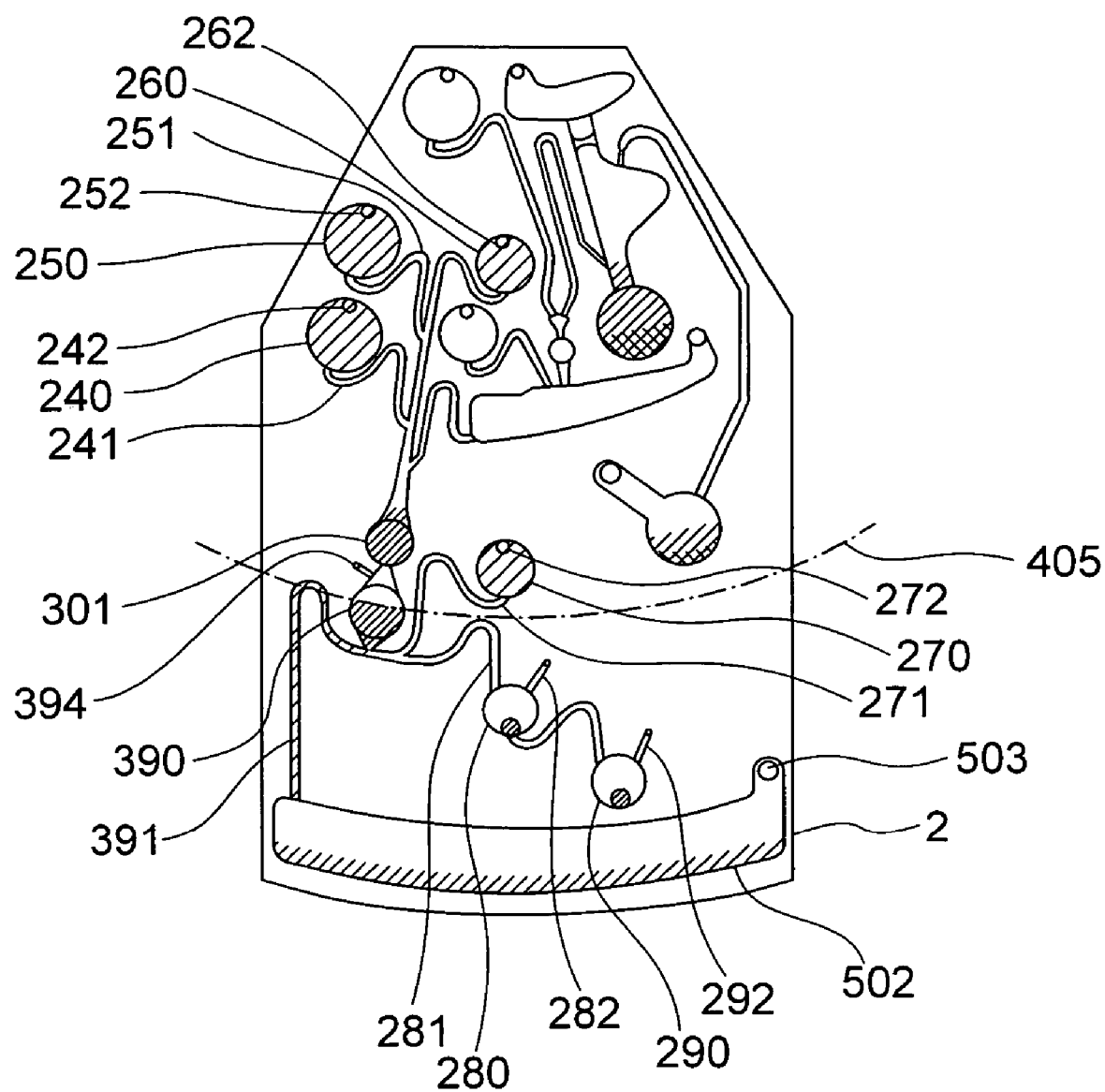
FIG. 12 is a view illustrating an operation of the examination cartridge according to the invention.

An explanation will be given to the washing process in STEP S400. An explanation will be given with reference to FIG. 12. The washing process includes first, second, and third washing processes. Firstly, an explanation will be given the first and second washing processes. The motor 11 is stopped, and the perforator 13 is used to perforate the cartridge cover 22 in that position, which corresponds to the vent hole 242 of the first washing-liquid vessel 240. Thereby, the first washing-liquid vessel 240 is connected to the atmosphere. When the motor 11 is rotated, the action of a centrifugal force causes the first washing-liquid to flow into the nucleic-acid trap part 301 through the first washing-liquid vessel outlet flow channel 241 from the first washing-liquid vessel 240 to wash unnecessary components, such as protein, etc., adhered to the nucleic-acid trap part 301. A waste liquid after washing flows out to the waste-liquid storage vessel 502 through the eluant recovery vessel outlet flow channel 391.

The motor 11 is stopped, and the perforator 13 is used to perforate the cartridge cover 22 in that position, which corresponds to the vent hole 252 of the second washing-liquid vessel 250. Thereby, the second washing-liquid vessel 250 is connected to the atmosphere. When the motor 11 is rotated, the action of the centrifugal force causes the second washing-liquid to flow into the nucleic-acid trap part 301 through the second washing-liquid vessel outlet flow channel 251 from the second washing-liquid vessel 250 to wash unnecessary components, such as salt, etc., adhered to the nucleic-acid trap part 301. A waste liquid after washing flows to the waste-liquid storage vessel 502 through the eluant recovery vessel outlet flow channel 391.

An explanation will be given the third washing process. The motor 11 is stopped, and the perforator 13 is used to perforate the cartridge cover 22 in that position, which corresponds to the vent hole 272 of the third washing-liquid vessel 270. Thereby, the third washing-liquid vessel 270 is connected to the atmosphere. When the motor 11 is rotated, the action of a centrifugal force causes the third washing-liquid to move toward the outer peripheral side through the third washing-liquid vessel outlet flow channel 271 from the third washing-liquid vessel 270 to fill the eluant recovery vessel outlet flow channel 391 and to flow back into the eluant recovery vessel 390. When all the third washing-liquid in the third washing-liquid vessel 270 flows out, a liquid level of the third washing-liquid in the eluant recovery vessel 390 and a liquid level in the eluant recovery vessel outlet flow channel 391 come to a radial position 405. An interior of the eluant recovery vessel 390 is washed by the third washing-liquid thus flowing back. A waste liquid after washing flows out to the waste-liquid storage vessel 502 through the eluant recovery vessel outlet flow channel 391. A process for elution of nucleic acids is executed subsequent to the washing process.

Figure 13:
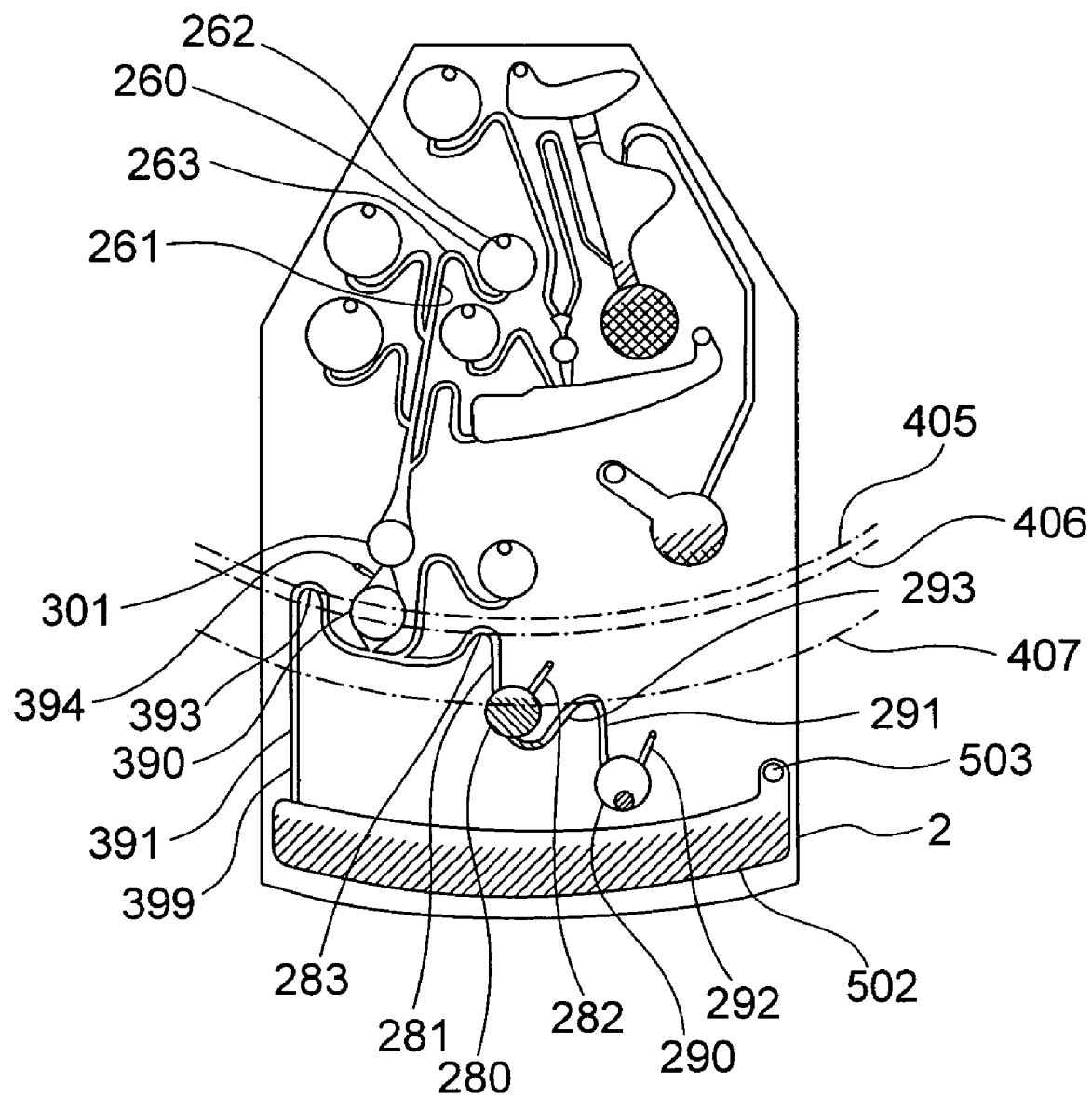
FIG. 13 is a view illustrating an operation of the examination cartridge according to the invention.

An explanation will be given to the process of elution and solution in STEP S500. As shown in FIG. 13, the motor 11 is stopped, and the perforator 13 is used to perforate the cartridge cover 22 in that position, which corresponds to the vent hole 262 of the eluant vessel 260. Thereby, the eluant vessel 260 is connected to the atmosphere. The perforator 13 is used to perforate the cartridge cover 22 in that position, which corresponds to the vent hole 282 of the first detection reagent vessel 280. Thereby, the first detection reagent vessel 280 is connected to the atmosphere. When the motor 11 is rotated, the action of the centrifugal force causes the eluant 661 to flow into the nucleic-acid trap part 301 through the outlet flow channel 261 from the eluant vessel 260. Nucleic acids trapped by the nucleic-acid trap part 301 are eluted by the eluant. The eluant containing the eluted nucleic acids flows into the eluant recovery vessel 390 from the nucleic-acid trap part 301.

Since a radial position 406 at an innermost periphery of the return portion 283 of the first detection liquid inflow channel 281 is positioned toward the outer peripheral side from the radial position 405 at an innermost periphery of the eluant recovery vessel outlet flow channel 391, an eluant having nucleic acids eluted therefrom passes through the first detection liquid inflow channel 281 to flow into the first detection reagent vessel 280 to dissolve the dry first detection reagent.

At this time, since the second detection reagent vessel 290 has not yet been connected to the atmosphere, the eluant having flowed into the first detection reagent vessel 280 cannot flow out to the second detection reagent vessel 290. That is, the eluant in the first detection reagent vessel 280 is held in the first detection reagent vessel 280 even when its liquid level is positioned toward the inner peripheral side from a radial position 407 at an innermost periphery of the return portion 293 of the second detection liquid inflow channel 291.

Figure 14:
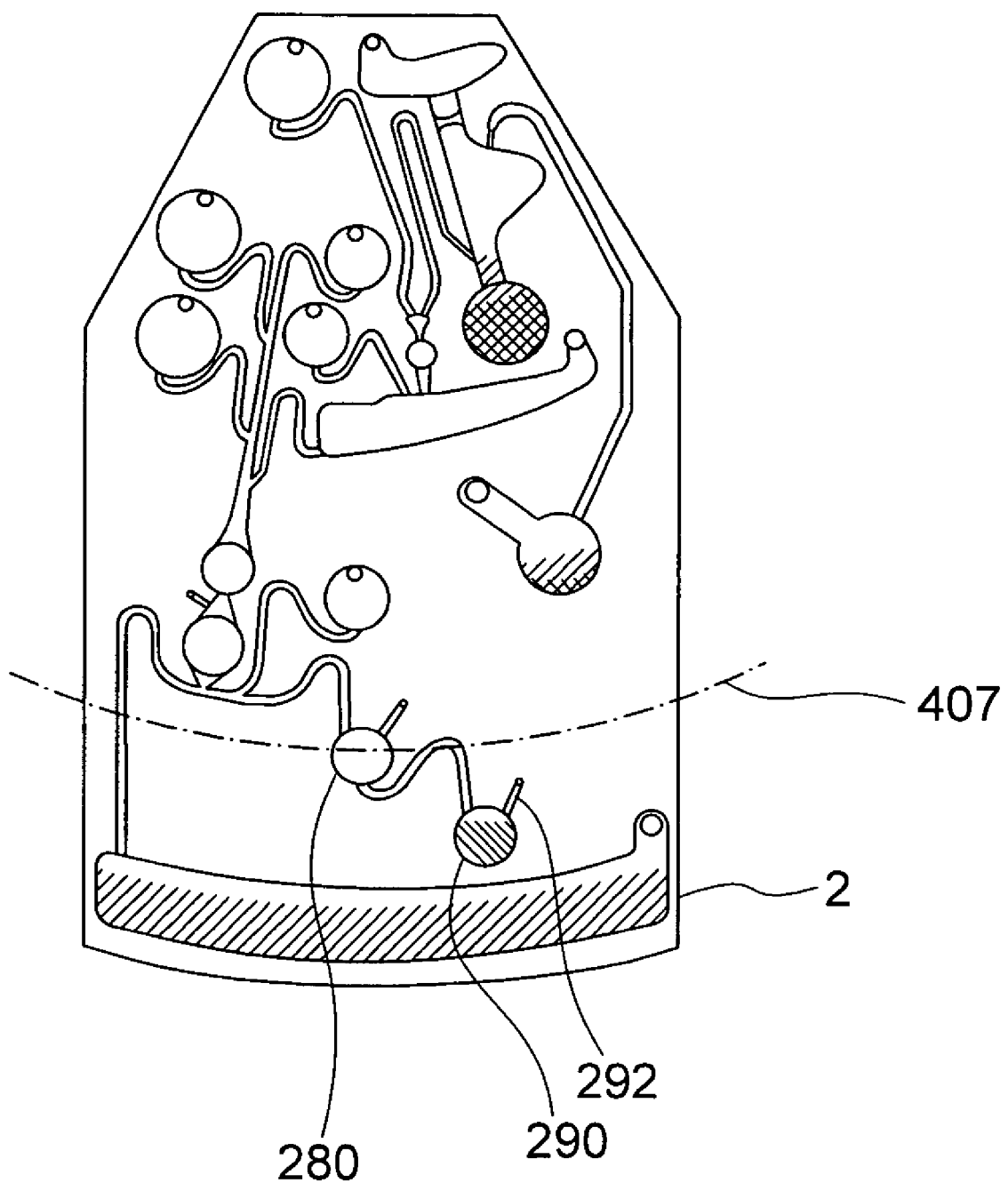
FIG. 14 is a view illustrating an operation of the examination cartridge according to the invention.

Finally, an explanation will be given to detection of solution in STEP S600. As shown in FIG. 14, the motor 11 is stopped, and the cartridge cover 22 is perforated in that position, which corresponds to the vent hole 292 of the second detection reagent vessel 290. Thereby, the second detection reagent vessel 290 is connected to the atmosphere. When the motor 11 is rotated, the action of the centrifugal force causes a liquid in the first detection reagent vessel 280 to flow into the second detection reagent vessel 290 through the second detection liquid inflow channel 291 to dissolve the dry second detection reagent.

According to a method of amplification and detection, the heating device 14 is used to irradiate light from above the first detection reagent vessel 280 or the second detection reagent vessel 290 to perform heating. Subsequently, the detection device 15 is moved onto the second detection reagent vessel 290 to detect, for example, a quantity of fluorescent emission.

According to the invention, an operation of dispensing a reagent is made needless and there occurs no contamination of a reagent due to deficiency in operation. Also, there is no need of providing any valve, which controls flow of respective reagents, midway a flow channel, any residual liquid is not generated in valve portions midway a flow channel, contamination by a reagent in a preceding process can be prevented, and specific components such as nucleic acid, etc. in a liquid specimen can be extracted in high purity and analyzed with high accuracy.

Figure 15:
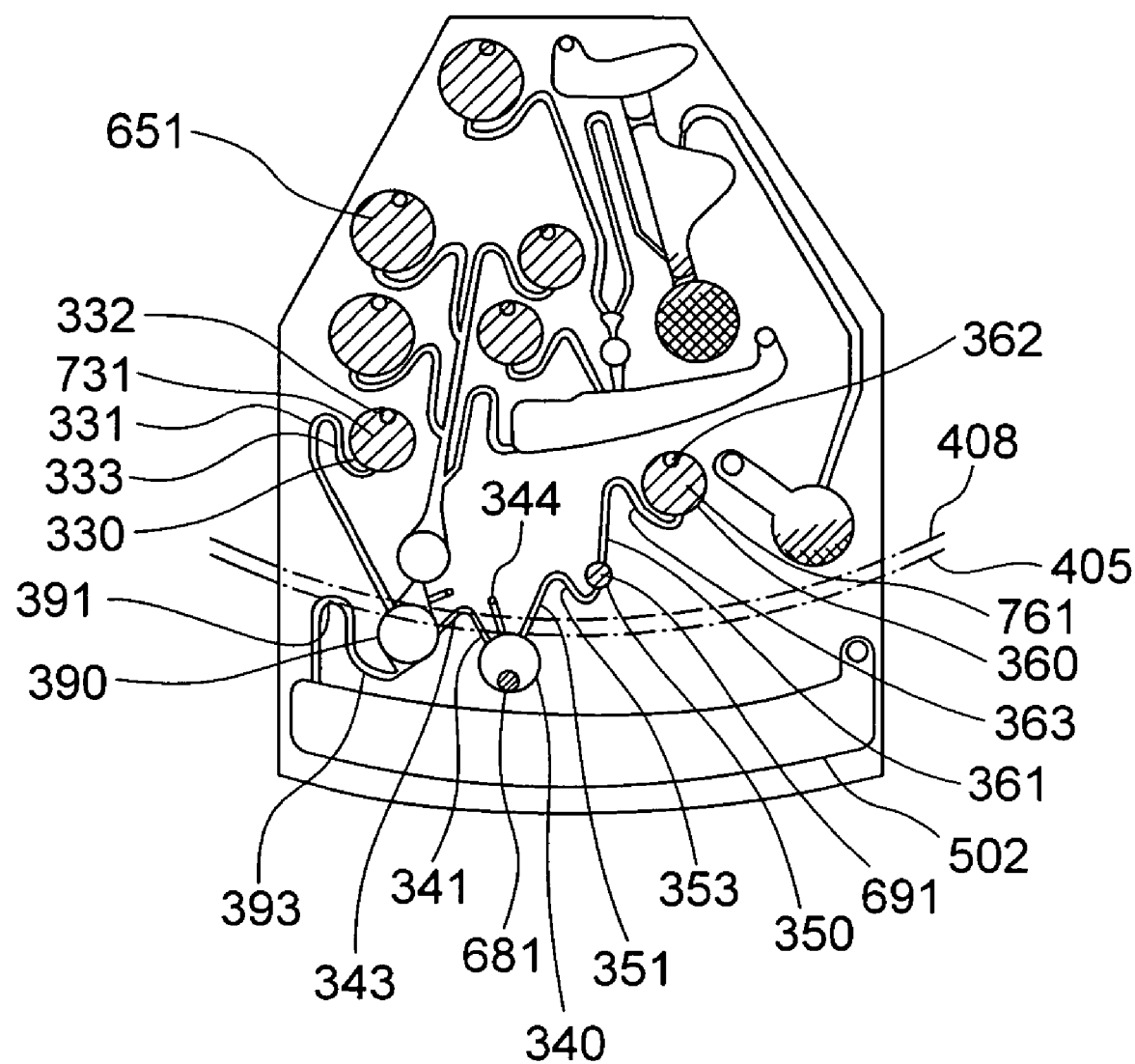
FIG. 15 is a view illustrating an operation of the examination cartridge according to the invention.

FIG. 15 is a further example of an examination cartridge according to the invention. As compared with the first example shown in FIGS. 6 to 14, the present example is different therefrom in that an expulsion liquid vessel 330 for storage of an expulsion liquid 731 is provided in place of the third washing-liquid vessel 270. The expulsion liquid 731 is a liquid, such as silicone oil, etc., which is larger in specific gravity than water and is not soluble in water. A further difference resides in that in place of the first detection reagent vessel 280 and the second detection reagent vessel 290, there are provided a detection vessel 340 for preservation of the dry first detection reagent 681, a second detection reagent vessel 350 for storage of the dry second detection reagent 691, and a second detection reagent dissolution reagent vessel 360 for storage of a second detection reagent dissolution reagent 761.

Provided between the expulsion liquid vessel 330 and the eluant recovery vessel 390 is an expulsion liquid vessel outlet flow channel 331 having a return portion 333 starting from an outer peripheral end of the expulsion liquid vessel 330, and extending toward the inner peripheral side, the expulsion liquid vessel outlet flow channel terminating at an inner peripheral end of the eluant recovery vessel 390. Provided between the eluant recovery vessel 390 and the detection vessel 340 is an eluant outflow channel 341 having a return portion 343 starting from the neighborhood of an inner peripheral end of the eluant recovery vessel 390, and extending toward the inner peripheral side, the eluant outflow channel terminating at an inner peripheral end of the detection vessel 340. Provided between the second detection liquid dissolution reagent vessel 360 and the dry second reagent vessel 350 is a second detection liquid dissolution reagent flow channel 361 having a return portion 363 starting from an outer peripheral end of the second detection liquid dissolution reagent vessel 360, and extending toward the inner peripheral side. Provided between the dry second reagent vessel 350 and the detection vessel 340 is a second reagent outflow channel 351 having a return portion 353 starting from an outer peripheral end of the dry second reagent vessel 350, and extending toward the inner peripheral side. A flow channel connected to an outer peripheral side of the eluant recovery vessel 390 comprises only the eluant recovery vessel outlet flow channel 391 having the return portion 393.

Operations up to the second washing process are the same as those in case of the first example shown in FIGS. 6 to 14. Since a radial position 408 at an innermost periphery of the return portion 343 of the eluant outflow channel 341 is positioned toward the inner peripheral side from the radial position 405 at an innermost periphery of the return portion 393 of the eluant recovery vessel outlet flow channel 391, the first and second washing liquids having flowed into the eluant recovery vessel 390 flows out to the waste-liquid storage vessel 502 through the eluant recovery vessel outlet flow channel 391.

In the present example, a process of filling the expulsion liquid 731 is performed instead of the third washing process. The motor 11 is stopped, and the perforator 13 is used to perforate the cartridge cover 22 in that position, which corresponds to the vent hole 332 of the expulsion liquid vessel 330. Thereby, the expulsion liquid vessel 330 is connected to the atmosphere. The eluant recovery vessel 390 has already been connected to the atmosphere.

Figure 16:
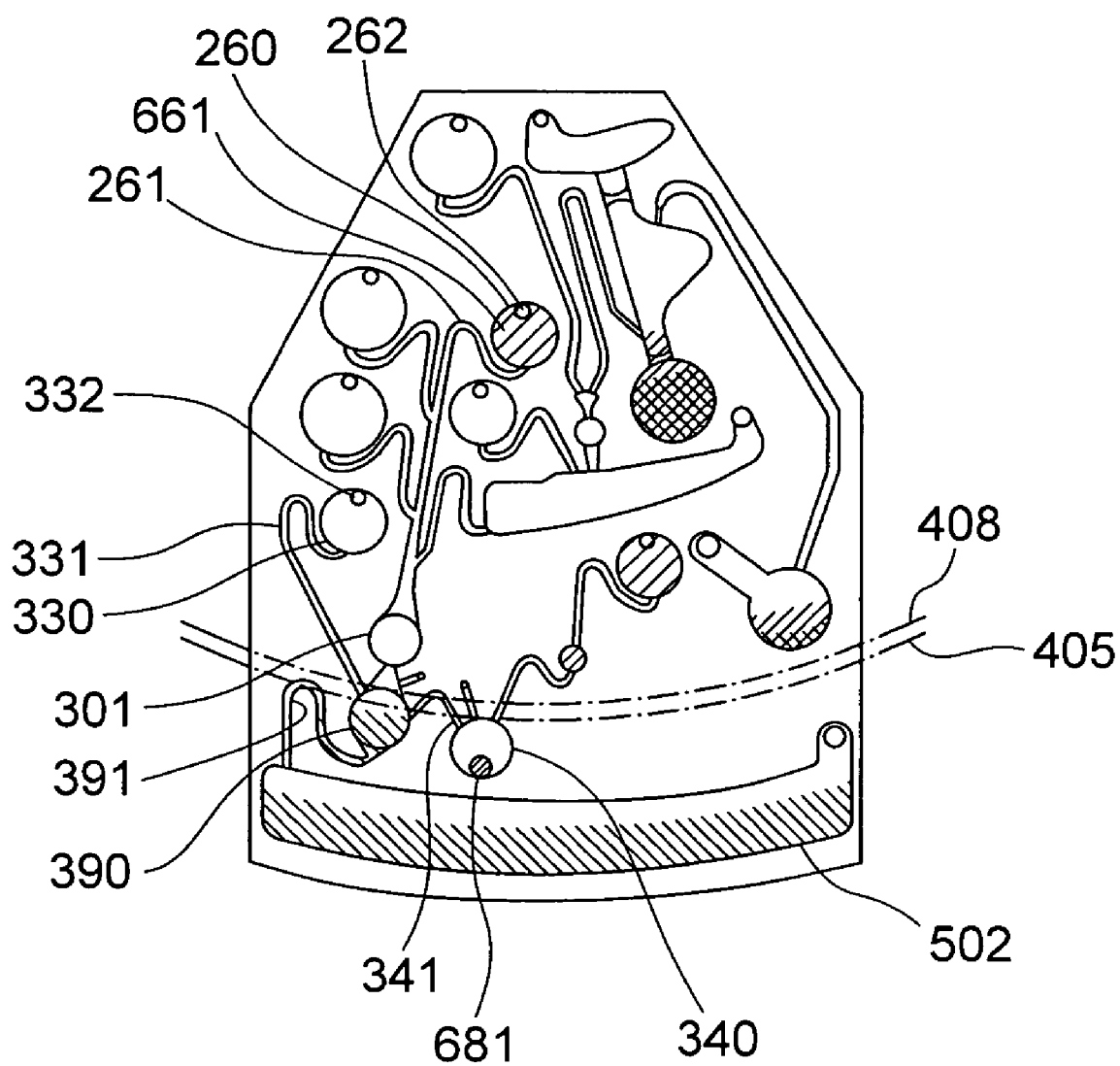
FIG. 16 is a view illustrating an operation of the examination cartridge according to the invention.

As shown in FIG. 16, when the motor 11 is rotated, the action of the centrifugal force causes the expulsion liquid 731 to flow into the eluant recovery vessel 390 through the outlet flow channel 331 from the expulsion liquid vessel 330. A connection of the eluant recovery vessel 390 and the eluant outflow channel 341 is positioned toward the outer peripheral side from the radial position 405 at the innermost periphery of the return portion 393 of the eluant recovery vessel outlet flow channel 391. A liquid amount of the expulsion liquid 731 is set so that when the expulsion liquid flows into the eluant recovery vessel 390, the liquid level comes just to a position of the connection. Accordingly, the expulsion liquid 731 having flowed into the eluant recovery vessel 390 remains in the eluant recovery vessel 390 and does not flow out through the eluant recovery vessel outlet flow channel 391.

An explanation will be given to the process of elution in STEP S500. The motor 11 is stopped, and the perforator 13 is used to perforate the cartridge cover 22 in that position, which corresponds to the vent hole 262 of the eluant vessel 260. Thereby, the eluant vessel 260 is connected to the atmosphere. When the motor 11 is rotated, the action of the centrifugal force causes the eluant 661 to flow into the nucleic-acid trap part 301 through the outlet flow channel 261 from the eluant vessel 260. Nucleic acids trapped by the nucleic-acid trap part 301 are eluted by the eluant. The eluant containing the eluted nucleic acids flows into the eluant recovery vessel 390 from the nucleic-acid trap part 301.

Figure 17:
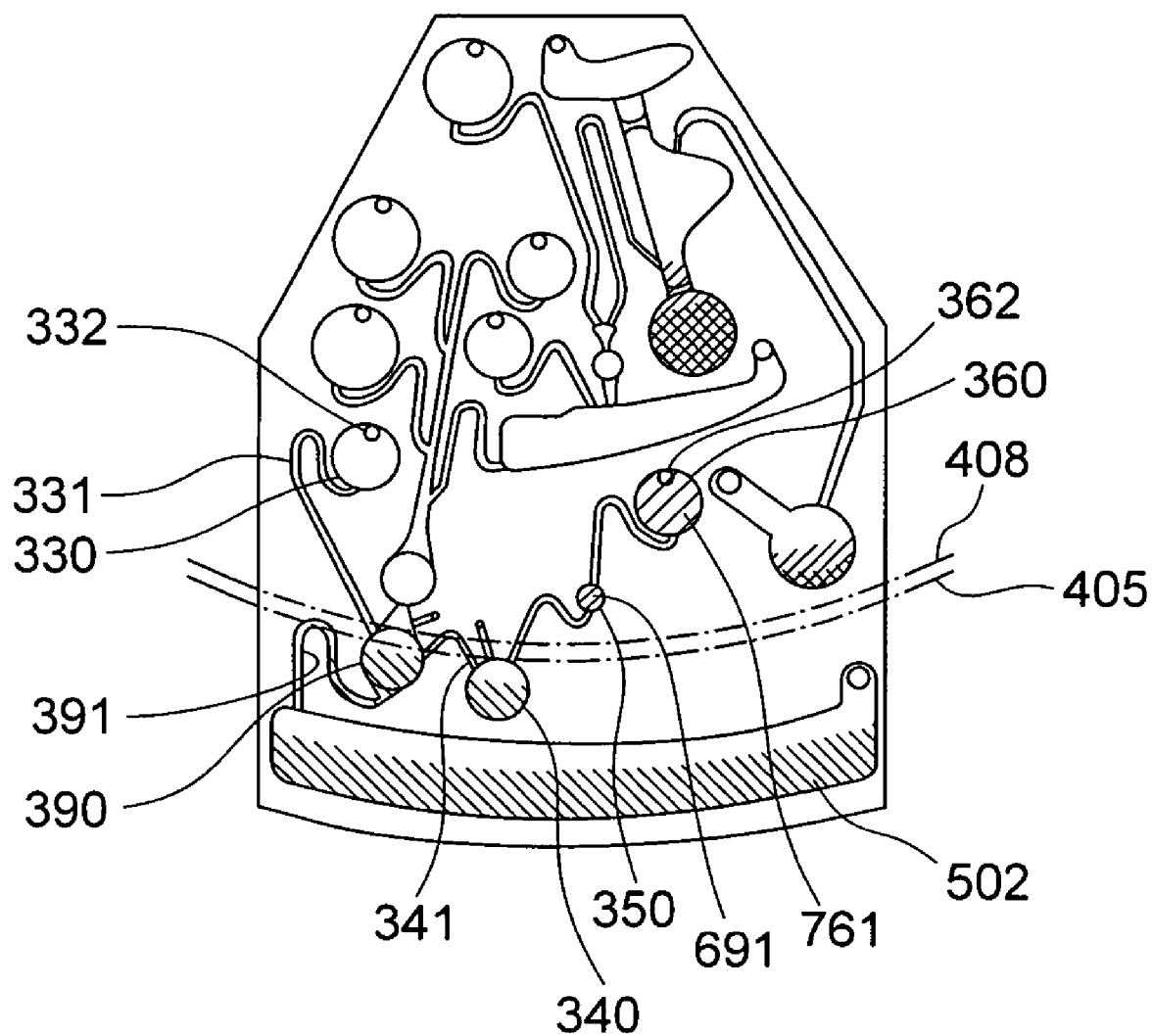
FIG. 17 is a view illustrating an operation of the examination cartridge according to the invention.

The expulsion liquid 731, which is larger in specific gravity than water and is not soluble in water, has already been filled in the eluant recovery vessel 390. Accordingly, as shown in FIG. 17, the eluant having flowed into the eluant recovery vessel 390 flows on the expulsion liquid 731 to flow to the detection vessel 340 through the eluant outflow channel 341 to dissolve the dry first detection reagent 681.

Figure 18:
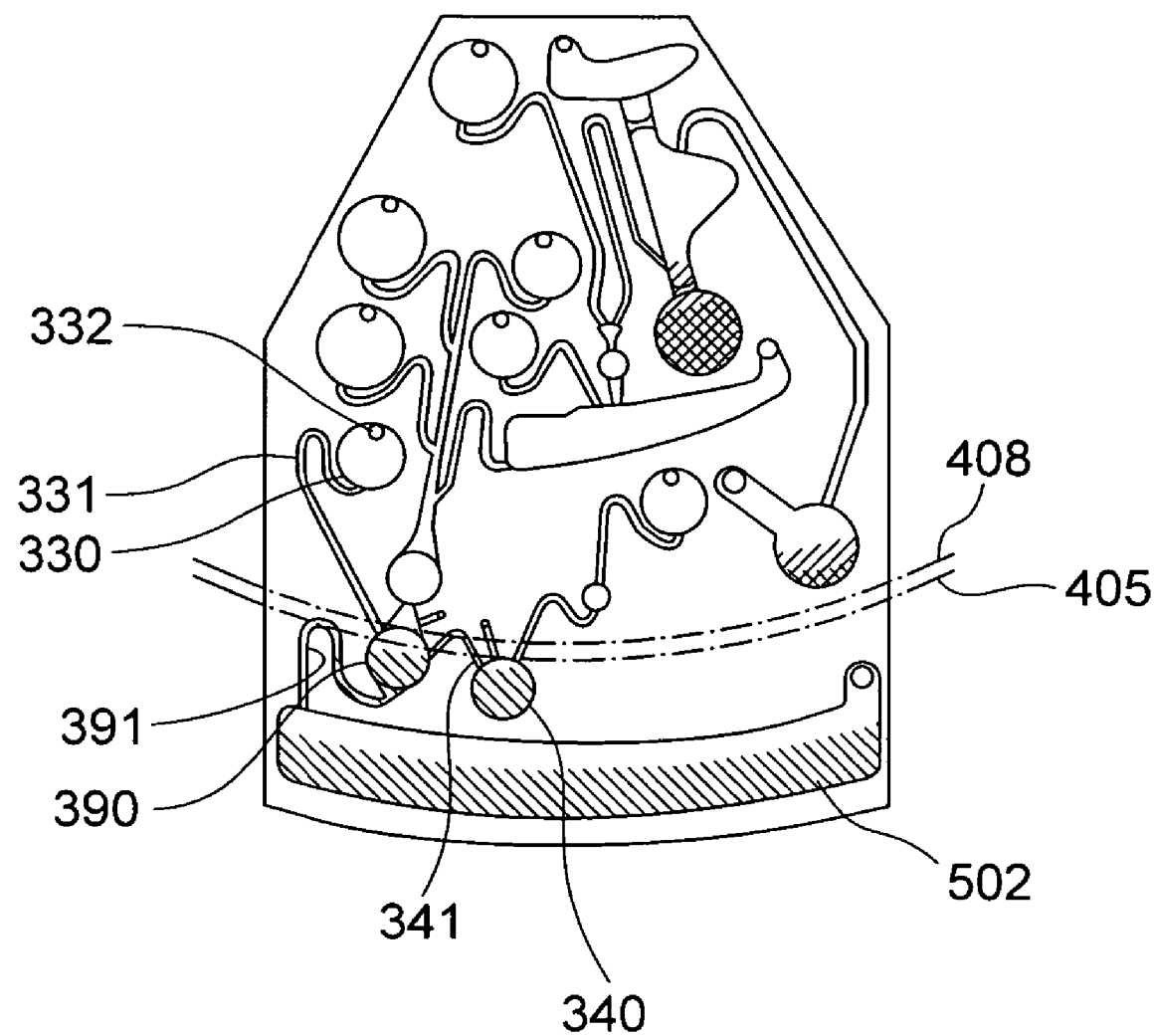
FIG. 18 is a view illustrating an operation of the examination cartridge according to the invention.

The motor 11 is stopped, and a vent hole 362 of the second detection liquid dissolution reagent vessel 360 is perforated. Thereby, the second detection liquid dissolution reagent vessel 360 is connected to the atmosphere. As shown in FIG. 18, when the motor 11 is rotated, the action of the centrifugal force causes the second detection reagent dissolution reagent 761 to flow out to the dry second reagent vessel 350 from the second detection liquid dissolution reagent vessel 360 to dissolve the second reagent 691. The second reagent 691 dissolved by the second detection reagent dissolution reagent 761 flows into the detection vessel 340 and mixes with the first reagent.

According to a method of amplification detection, the heating device 14 is used to irradiate light from above the detection vessel 340 to perform heating. Subsequently, the detection device 15 is moved onto the detection vessel 340 to detect, for example, a quantity of fluorescent emission.

According to the invention, an operation of dispensing a reagent is made needless and there is no fear of contamination of a reagent due to deficiency in operation. Also, there is no need of providing any valve, which controls flow of respective reagents, midway a flow channel, any residual liquid is not generated in valve portions midway a flow channel, contamination by a reagent in a preceding process can be prevented, and specific components such as nucleic acid, etc. in a liquid specimen can be extracted in high purity and analyzed with high accuracy.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A chemical analysis apparatus comprising: a holding disk rotatable about an axis of rotation, which passes through a center of the disk; and an examination cartridge held by the holding disk to be removable, the examination cartridge comprising: a substrate including a vessel and a flow channel, which are defined by recesses; and a cover that covers the vessel and the flow channel, a centrifugal force generated by rotation of the holding disk being made use of to move a solution from a vessel on an inner peripheral side relative to the axis of rotation to a vessel on an outer peripheral side relative to the axis of rotation through the flow channel, and a perforator that perforates successively the vessels in the examination cartridges wherein the substrate is provided with a specimen vessel that accommodates a specimen, a trap part that traps a specific substance contained in the specimen, an eluant vessel that accommodates an eluant to elute the substance trapped by the trap part, an eluant recovery vessel that accommodates an eluant containing the substance discharged from the trap part, a first detection vessel that preserves a dry detection reagent and holds an eluant containing the substance from the eluant recovery vessel to detect the substance, and a waste-liquid storage vessel that recovers a solution discharged through the trap part and the eluant recovery vessel, a waste-liquid outflow channel terminating at an inner peripheral end of the waste-liquid storage vessel through a return portion starting from an outer peripheral end of the eluant recovery vessel, extending toward the inner peripheral side, and again extending toward the outer peripheral side is provided between the eluant recovery vessel on the inner peripheral side and the waste-liquid storage vessel on the outer peripheral side, and an eluant outflow channel terminating at an inner peripheral end of the first detection vessel through a return portion starting from an outer peripheral end of the eluant recovery vessel, extending toward the inner peripheral side, and again extending toward the outer peripheral side is provided between the eluant recovery vessel on the inner peripheral side and the first detection vessel on the outer peripheral side.

2. A chemical analysis apparatus according to claim 1, wherein an innermost peripheral position of the return portion of the waste-liquid outflow channel is positioned toward the inner peripheral side from an innermost peripheral position of the eluant outflow channel, whereby an eluant from the eluant vessel passes through the trap part to be led to the eluant recovery vessel to be further led to the first detection vessel through the eluant outflow channel.

3. A chemical analysis apparatus according to claim 1, wherein the substrate is provided with a trap part washing-liquid vessel that accommodates a washing liquid to wash the trap part, and the examination cartridge is structured so that a washing liquid from the trap part washing-liquid vessel is led to the waste-liquid storage vessel through the trap part, the eluant recovery vessel, and the waste-liquid outflow channel without the first detection vessel being connected to the atmosphere but sealed.

4. A chemical analysis apparatus according to claim 1, wherein the substrate is provided with an eluant recovery vessel washing-liquid vessel that accommodates a washing liquid to wash the eluant recovery vessel, and the examination cartridge is structured so that a washing liquid from the eluant recovery vessel washing-liquid vessel is led to the eluant recovery vessel and further led to the waste-liquid storage vessel through the waste-liquid outflow channel without the first detection vessel being connected to the atmosphere but sealed.

5. A chemical analysis apparatus according to claim 1, wherein the first detection vessel contains a dried first examination reagent and is structured so that the first examination reagent is dissolved by an eluant introduced into the first detection vessel.

6. A chemical analysis apparatus according to claim 5, further comprising: a second detection vessel provided toward the outer peripheral side from the first detection vessel to accommodate a dried second examination reagent; and an examination reagent outflow channel terminating at an inner peripheral end of the second detection vessel through a return portion starting from an outer peripheral end of the first detection vessel, extending toward the inner peripheral side, and again extending toward the outer peripheral side, and wherein the examination cartridge is structured so that an eluant having dissolved the first examination reagent from the first detection vessel is led to the second detection vessel through the examination reagent outflow channel and an eluant introduced into the second detection vessel dissolves the second examination reagent.

7. A chemical analysis apparatus according to claim 1, further comprising: a heating device that heats a solution in the first detection vessel, and a detection device that detects a predetermined substance from the solution in the first detection vessel.

8. A chemical analysis cartridge comprising: a substrate including a vessel and a flow channel, which are defined by recesses; and a cover that covers the vessel and the flow channel, a centrifugal force generated by rotation about an axis of rotation perpendicular to the substrate being made use of to move a solution from a vessel on an inner peripheral side relative to the axis of rotation to a vessel on an outer peripheral side relative to the axis of rotation through the flow channel, and a perforator that perforates successively the vessels in the examination cartridges, wherein the substrate is provided with a specimen vessel that accommodates a specimen, a trap part that traps a specific substance contained in the specimen, an eluant vessel that accommodates an eluant to elute the substance trapped by the trap part, an eluant recovery vessel that accommodates an eluant containing the substance discharged from the trap part, a detection vessel that preserves a dry detection reagent and holds an eluant containing the substance from the eluant recovery vessel to detect the substance, and a waste-liquid storage vessel that recovers a solution discharged through the trap part and the eluant recovery vessel, a waste-liquid outflow channel terminating at an inner peripheral end of the waste-liquid storage vessel through a return portion starting from an outer peripheral end of the eluant recovery vessel, extending toward the inner peripheral side, and again extending toward the outer peripheral side is provided between the eluant recovery vessel on the inner peripheral side and the waste-liquid storage vessel on the outer peripheral side, and an eluant outflow channel terminating at an inner peripheral end of the detection vessel through a return portion starting from an outer peripheral end of the eluant recovery vessel, extending toward the inner peripheral side, and again extending toward the outer peripheral side is provided between the eluant recovery vessel on the inner peripheral side and the detection vessel on the outer peripheral side.

\* \* \* \* \*